United States Patent
Cho

(10) Patent No.: US 9,795,344 B2
(45) Date of Patent: *Oct. 24, 2017

(54) RADIATION IMAGING APPARATUS, COMPUTED TOMOGRAPHY APPARATUS, AND RADIATION IMAGING METHOD

(71) Applicant: SAMSUNG ELECTRONICS CO., LTD., Suwon-si (KR)

(72) Inventor: Min Kook Cho, Busan (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/324,418

(22) Filed: Jul. 7, 2014

(65) Prior Publication Data

US 2014/0321611 A1    Oct. 30, 2014

Related U.S. Application Data

(63) Continuation of application No. 13/946,381, filed on Jul. 19, 2013, now Pat. No. 8,798,230.

(30) Foreign Application Priority Data

Nov. 19, 2012 (KR) .................. 10-2012-0131082
Apr. 26, 2013 (KR) .................. 10-2013-0046722

(51) Int. Cl.
*A61B 6/03* (2006.01)
*A61B 6/06* (2006.01)
*A61B 6/00* (2006.01)

(52) U.S. Cl.
CPC ............ *A61B 6/032* (2013.01); *A61B 6/03* (2013.01); *A61B 6/06* (2013.01); *A61B 6/405* (2013.01); *A61B 6/4035* (2013.01); *A61B 6/542* (2013.01)

(58) Field of Classification Search
CPC ....... A61B 6/405; A61B 6/4035; A61B 6/542; A61B 6/03; A61B 6/027; A61B 6/4085;
(Continued)

(56) References Cited

U.S. PATENT DOCUMENTS

| 2,790,912 A | * | 4/1957 | Graves et al. | H05G 1/36 378/157 |
| 4,200,800 A | * | 4/1980 | Swift | H05G 1/34 378/150 |
| 4,339,799 A | * | 7/1982 | Abele | A61B 6/032 378/11 |
| 5,025,463 A | * | 6/1991 | Saito | A61B 6/032 378/19 |

(Continued)

FOREIGN PATENT DOCUMENTS

| CN | 1309949 A | 8/2001 |
| CN | 102427767 A | 4/2012 |

(Continued)

OTHER PUBLICATIONS

Communication, Issued by the Korean Intellectual Property Office, Dated Aug. 26, 2014, In counterpart Korean Application No. 10-2013-0046722.

(Continued)

*Primary Examiner* — Glen Kao
*Assistant Examiner* — Chi-Cheng Kao
(74) *Attorney, Agent, or Firm* — Sughrue Mion, PLLC

(57) ABSTRACT

An emitter is configured to move around the object and to emit radiation toward an object. A controller is configured to control the emitter to stop a radiation emission, when the emitter is located in a radiation reception zone in which the radiation emitted by the emitter is received or in which the radiation emitted by the emitter is supposed to be received.

20 Claims, 49 Drawing Sheets

(58) Field of Classification Search
CPC ....... A61B 6/482; A61B 6/5205; A61B 6/583; A61B 6/5217; A61B 6/4233; A61B 6/469; A61B 6/488; A61B 6/5258; A61B 6/502; A61B 6/503; A61B 6/507; A61B 6/545; A61B 6/032
USPC .......................... 378/4, 19, 15, 156–160, 57
See application file for complete search history.

(56) References Cited

U.S. PATENT DOCUMENTS

| | | | |
|---|---|---|---|
| 6,298,111 B1 * | 10/2001 | Ozaki | A61B 6/541 378/114 |
| 6,968,040 B2 | 11/2005 | Van Woezik | |
| 7,123,680 B2 * | 10/2006 | Katada | A61B 6/032 378/16 |
| 8,279,999 B2 | 10/2012 | Kondo et al. | |
| 8,798,230 B2 * | 8/2014 | Cho | 378/19 |
| 2001/0019599 A1 | 9/2001 | Guendel | |
| 2009/0238327 A1 | 9/2009 | Heuscher et al. | |
| 2011/0286574 A1 | 11/2011 | Suzuki | |
| 2012/0128120 A1 | 5/2012 | De Man et al. | |
| 2012/0177172 A1 | 7/2012 | Ooshima | |

FOREIGN PATENT DOCUMENTS

| | | |
|---|---|---|
| CN | 102711619 A | 10/2012 |
| JP | 2009-89771 A | 4/2009 |
| JP | 2011-136027 A | 7/2011 |
| JP | 2011136027 A | 7/2011 |
| KR | 10-2009-0025927 A | 3/2009 |
| WO | 2010/133994 A1 | 11/2010 |

OTHER PUBLICATIONS

Extended European Search Report dated Jan. 8, 2014 issued in corresponding European Patent Application No. 13193339.
International Search Report dated Feb. 27, 2014 issued in corresponding International Patent Application No. PCT/KR2013/010486.
Communication issued on Oct. 19, 2015 by the European Patent Office in related Application No. 13193339.2.
Communication dated Jan. 7, 2016, issued by the State Intellectual Property Office of P.R. China in counterpart Chinese Application No. 201310585689.4.
Communication dated Sep. 21, 2016, issued by the European Patent Office in counterpart European Application No. 13193339.2.
Communication dated Sep. 20, 2016, issued by the State Intellectual Property Office of P.R. China in counterpart Chinese Application No. 201310585689.4.
Communication dated Dec. 27, 2016 issued by the State Intellectual Property Office of P.R. China in counterpart Chinese Patent Application No. 201310585689.4.
Communication dated Mar. 3, 2017 issued by the European Patent Office in counterpart European Patent Application No. 13 193 339.2.

* cited by examiner

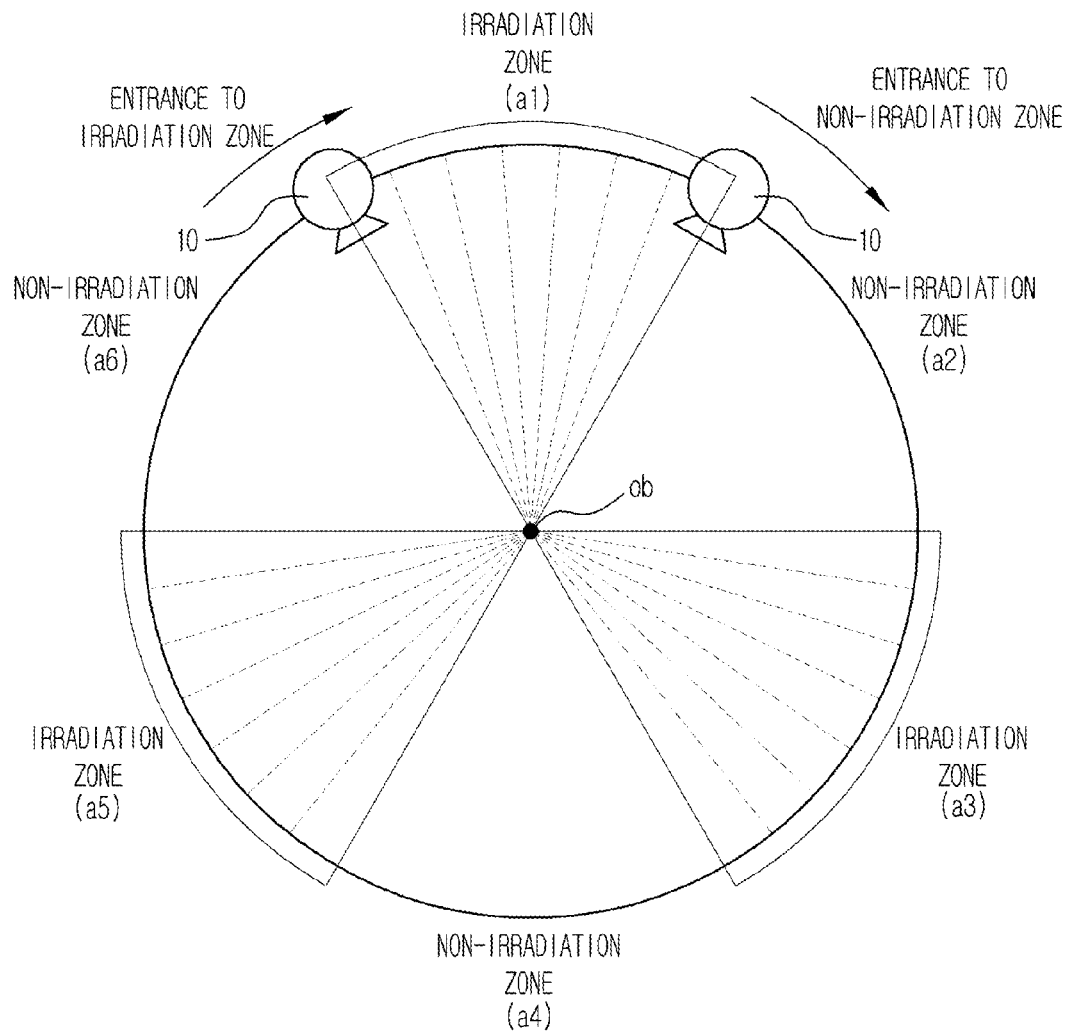

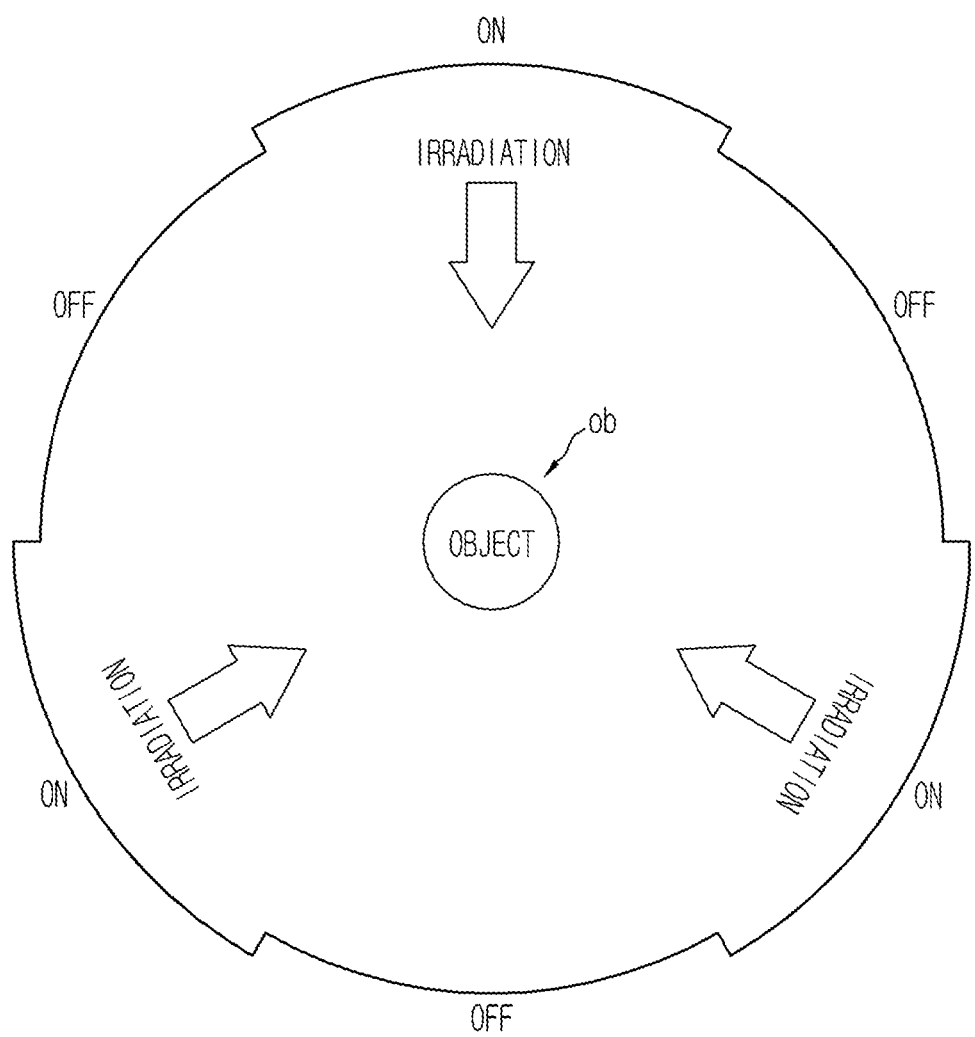

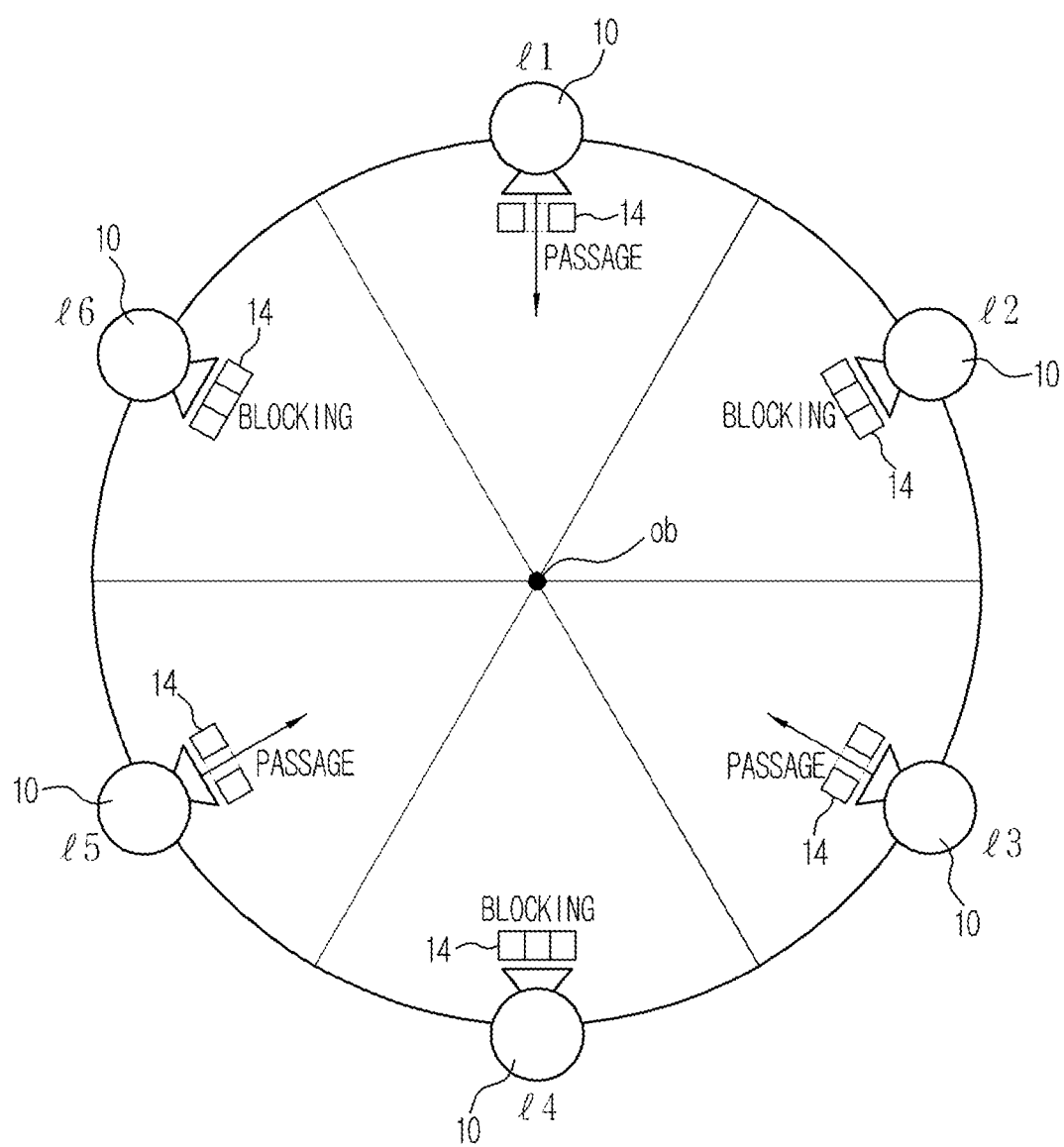

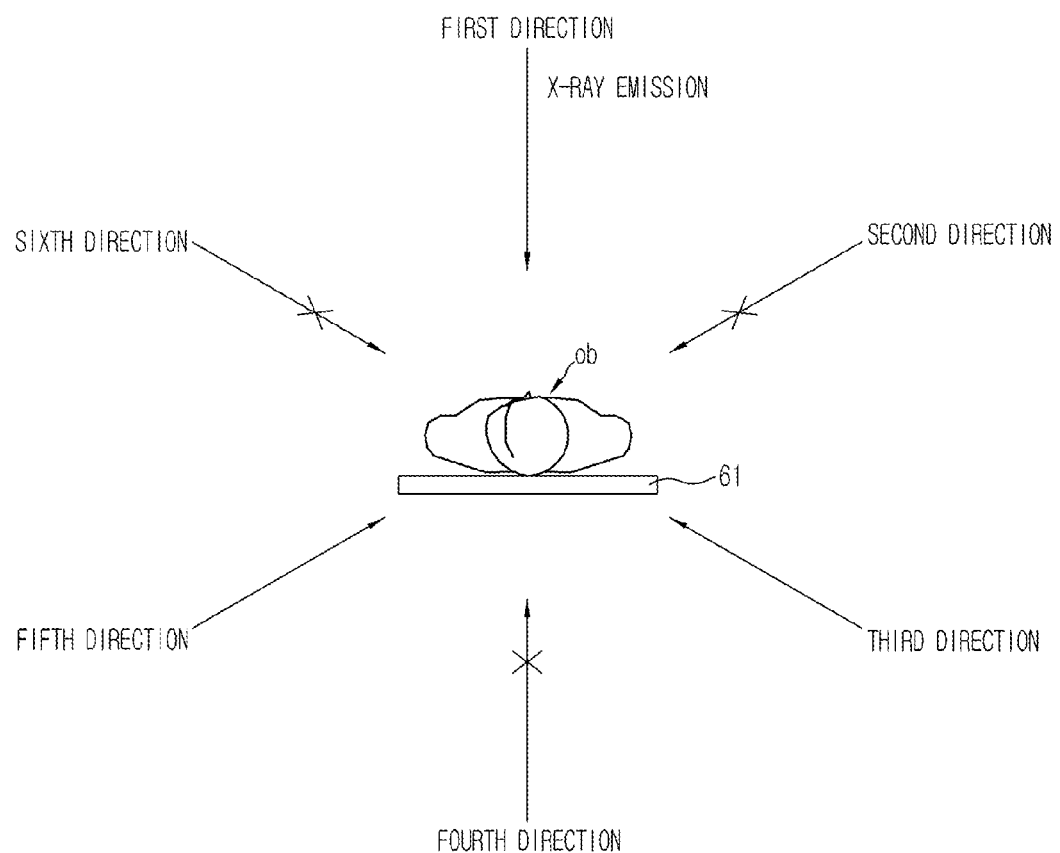

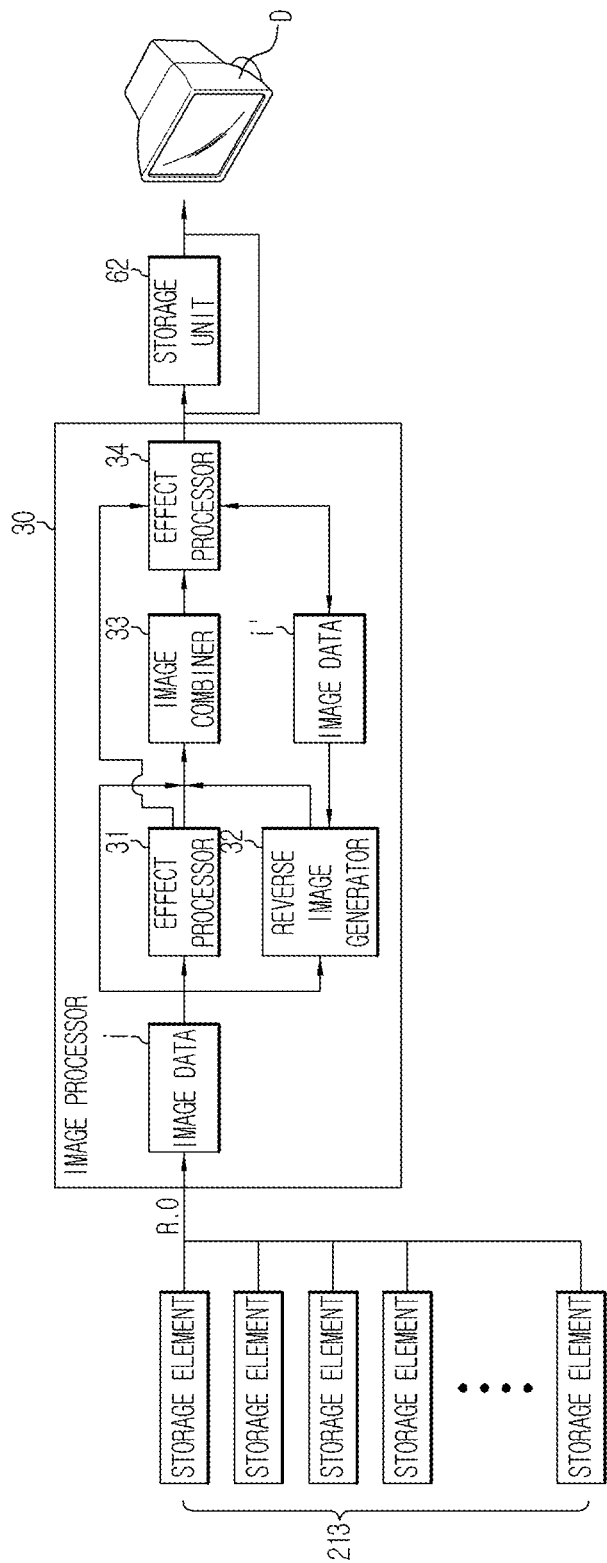

FIG.12F
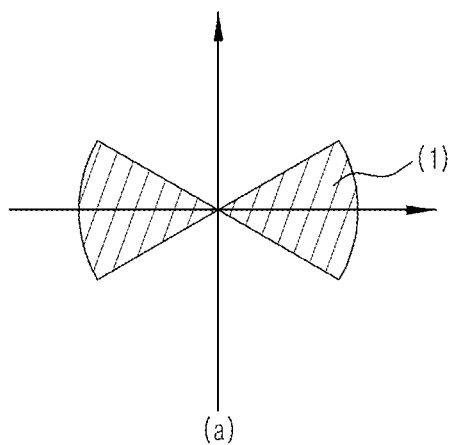
(a)
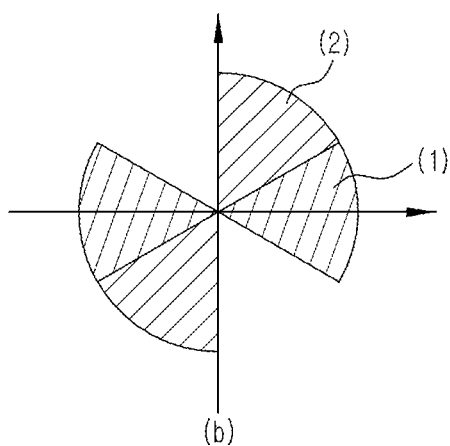
(b)
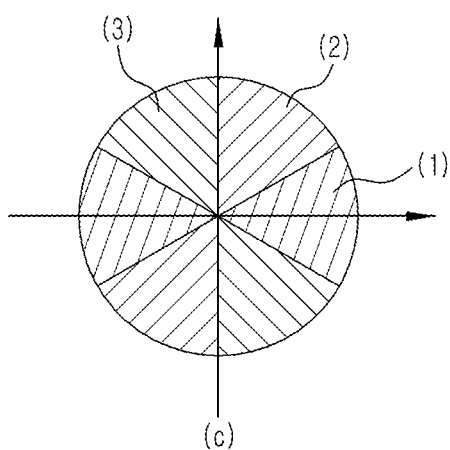
(c)

RADIATION IMAGING APPARATUS, COMPUTED TOMOGRAPHY APPARATUS, AND RADIATION IMAGING METHOD

CROSS-REFERENCE TO RELATED APPLICATIONS

This is a continuation of application Ser. No. 13/946,381 filed on Jul. 19, 2013 (now issued as U.S. Pat. No. 8,798, 230), which claims priority from Korean Patent Application No. 10-2012-0131082 filed on Nov. 19, 2012, and Korean Patent Application No. 10-2013-0046722 filed on Apr. 26, 2013, in the Korean Intellectual Property Office, the entire disclosures of which are incorporated herein by reference.

BACKGROUND

1. Field

Exemplary embodiments relate to a radiation imaging apparatus, a computed tomography apparatus, and a radiation imaging method using the same.

2. Description of the Related Art

A radiation imaging apparatus, such as a Digital Radiography (DR) system, a Computed Tomography (CT) apparatus, a Full Field Digital Mammography (FFDM) apparatus, or the like, is an imaging system that emits radiation, e.g., X-rays (also referred to as Roentgen rays) to an object, such as a human body or a part thereof or luggage, thereby acquiring an image of the object, for example, an image of internal materials, tissues or structures of the object.

The radiation imaging apparatus may be used in a medical imaging system to detect any diseases or other abnormalities of a human body, may be used to observe internal structures of components, and may be used as a scanner to scan luggage in the airport, etc.

A CT apparatus is adapted to acquire a plurality of cross-sectional images of an object by continuously emitting radiation to the object from around the object throughout 360 degrees and detecting radiation having passed through the object. To acquire successive cross-sectional images, the CT apparatus continuously emits radiation to the object, e.g., a human body from the beginning to the end of imaging.

SUMMARY

It is an aspect to provide a radiation imaging apparatus, a computed tomography apparatus, and a radiation imaging method, which enable acquisition of radiological images of an entire object via emission of radiation to the object in some directions or zones in the vicinity of the object.

It is another aspect to provide a computed tomography apparatus which enables generation of successive cross-sectional images of an object via radiation emission in some positions or zones.

It is a further aspect to considerably reduce radiation exposure of an object via radiation emission in some directions or zones.

Additional aspects will be set forth in part in the description which follows and, in part, will be obvious from the description.

In accordance with one aspect, a radiation imaging apparatus includes a radiation emitter to emit radiation to an object while moving around the object, a radiation detector to detect radiation emitted from the radiation emitter and change the detected radiation into an electric signal to thereby store the electric signal, and an irradiation controller to control the radiation emitter such that radiation is emitted to the object in at least one position around the object and such that no radiation is emitted to the object in a position corresponding to the at least one position.

The irradiation controller may control the radiation emitter such that the radiation emitter emits radiation to the object if the radiation emitter is located in the at least one position around the object and such that the radiation emitter stops radiation emission if the radiation emitter is located in a position opposite to the at least one radiation emission position.

The radiation imaging apparatus may further include an image processor to read out a radiological image from the electric signal changed by the radiation detector.

The image processor may generate at least one radiological image captured in a direction opposite to a radiation emission direction based on a single radiological image captured in the radiation emission direction.

The radiation emitter may move around the object at a preset angular speed. In this case, the irradiation controller may determine whether or not to perform radiation emission by the radiation emitter based on the angular speed of the radiation emitter, and may control radiation emission by the radiation emitter based on the determined result. In addition, the irradiation controller may control the radiation emitter such that the radiation emitter stops radiation emission when an irradiation duration has passed after radiation emission has begun, and such that the radiation emitter initiates radiation emission after a non-irradiation duration has passed after radiation emission has stopped.

The radiation imaging apparatus may further include a filter installed in a radiation emission path, along which radiation is emitted by the radiation emitter, to pass or block radiation emitted from the radiation emitter. Here, the irradiation controller may control the filter such that the filter passes radiation emitted from the radiation emitter if the radiation emitter reaches a given position while moving around the object and such that the filter blocks radiation emitted from the radiation emitter if the radiation emitter reaches a position or zone opposite to the given position about the object.

In accordance with another aspect, a radiation imaging apparatus includes a radiation emitter configured to move along a movement path defined around an object and to emit radiation to the object during movement thereof, and a radiation detector to receive radiation emitted from the radiation emitter and change the received radiation into an electric signal, wherein the movement path defined around the object is divided into at least one irradiation zone in which the radiation emitter emits radiation, and at least one non-irradiation zone in which the radiation emitter does not emit radiation, and the non-irradiation zone is located opposite to the at least one irradiation zone.

The radiation imaging apparatus may further include an image processor to generate a radiological image by combining at least one radiological image generated via detection of radiation emitted in the at least one irradiation zone.

The image processor may generate a radiological image of the non-irradiation zone opposite to the irradiation zone based on the radiological image of the irradiation zone.

The irradiation zone or the non-irradiation zone may be determined by an arc between at least two positions on the movement path.

The irradiation zone and the non-irradiation zone on the movement path may be alternatingly arranged.

The radiation emitter may be moved along the movement path defined around the object at a preset angular speed.

The radiation imaging apparatus may further include an irradiation controller to control the radiation emitter such that the radiation emitter initiates radiation emission when entering the irradiation zone and stops radiation emission when entering the non-irradiation zone.

The radiation emitter may be moved along the movement path defined around the object at a preset angular speed, and the irradiation controller may determine whether or not to perform radiation emission by the radiation emitter based on the angular speed of the radiation emitter, and may control radiation emission by the radiation emitter based on the determined result.

The irradiation controller may control the radiation emitter such that the radiation emitter stops radiation emission when an irradiation duration has passed after radiation emission has begun, and such that the radiation emitter initiates radiation emission after a non-irradiation duration has passed after radiation emission has stopped.

In accordance with another aspect, a radiation imaging apparatus includes a radiation emitter configured to move along a movement path defined around an object and to emit radiation to the object, a filter installed in a radiation emission path, along which radiation is emitted by the radiation emitter, to pass or block radiation emitted from the radiation emitter, and a radiation detector to receive radiation emitted from the radiation emitter and change the received radiation into an electric signal, wherein the filter passes radiation emitted from the radiation emitter in at least one irradiation position or irradiation zone on the movement path, and blocks radiation emitted from the radiation emitter in at least one non-irradiation position or non-irradiation zone corresponding to the at least one irradiation position or irradiation zone.

The radiation imaging apparatus may further include an image processor to read out a radiological image from the electric signal changed from the radiation emitted in the at least one irradiation position or irradiation zone. The image processor may generate a radiological image of the at least one non-irradiation position or non-irradiation zone based on the radiological image of the at least one irradiation position or irradiation zone.

The irradiation position or irradiation zone and the non-irradiation position or non-irradiation zone on the movement path may be alternatingly arranged.

The movement path defined around the object may be circular or spiral.

The filter may include at least one opening to pass radiation.

The filter may rotate about a rotating shaft located inside or outside of the filter. In this case, the filter may rotate at an angular speed corresponding to an angular speed of the radiation emitter that moves along a circular or spiral movement path. In addition, the angular speed of the filter may be determined based on the number of openings formed in the filter to pass radiation, the angular speed of the radiation emitter, the number of times radiation is emitted while the radiation emitter rotates once, or the size of the irradiation zone or the non-irradiation zone.

In accordance with another aspect, a radiation imaging apparatus includes a radiation emitter configured to move around an object at least one time and to generate radiation upon receiving power applied thereto and emit the generated radiation to the object, a radiation detector configured to move around the object at least one time according to movement of the radiation emitter and to detect radiation emitted from the radiation emitter and change the detected radiation into an electric signal to thereby store the electric signal, and an irradiation controller to control application or interception of power to the radiation emitter, wherein the irradiation controller performs application and interception of power to the radiation emitter plural times while the radiation emitter and the radiation detector move around the object once.

In accordance with another aspect, a radiation imaging apparatus includes a radiation emitter configured to move around an object and to emit radiation to the object, a radiation detector to detect radiation emitted from the radiation emitter and change the detected radiation into an electric signal to thereby store the electric signal, and an irradiation controller to control the radiation emitter such that radiation is emitted to the object in a given direction of the object and such that no radiation is emitted to the object in a direction corresponding to the given direction in which radiation is emitted to the object.

In accordance with another aspect, a computed tomography apparatus includes a rotatable gantry, a radiation emitter installed at one side of the gantry to emit radiation to an object, a cradle on which the object is placed, the cradle being moved into the gantry, and a radiation detector installed to the gantry at an opposite side of the radiation emitter and serving to receive radiation having passed through the object placed on the cradle and change the received radiation into an electric signal, wherein the radiation emitter emits radiation to the object in a given direction of the object and does not emit radiation to the object in a direction opposite to the given direction.

The computed tomography apparatus may further include an irradiation controller to control the radiation emitter such that the radiation emitter emits radiation when located in a given position while moving around the object and to block radiation emission by the radiation emitter when the radiation emitter is located in a position corresponding to the given position.

The radiation emitter may move around the object at a preset angular speed, and the irradiation controller may determine whether or not to perform radiation emission by the radiation emitter based on the angular speed of the radiation emitter, and may control the radiation emission by the radiation emitter based on the determined result.

The irradiation controller may stop radiation emission by the radiation emitter when an irradiation duration has passed after radiation emission has begun, and may initiate radiation emission by the radiation emitter after a non-irradiation duration has passed after radiation emission has stopped.

The radiation emitter may move around the object at a preset angular speed.

The computed tomography apparatus may further include an image processor to read out a radiological image from the electric signal changed by the radiation detector.

The image processor may generate at least one radiological image captured in a direction opposite to a radiation emission direction based on a single radiological image captured in the radiation emission direction.

The image processor may generate at least one intermediate radiological image between a plurality of radiological images acquired when emitting radiation plural times in the same direction.

The image processor may generate at least one radiological image captured in a direction opposite to a radiation emission direction based on the generated at least one intermediate radiological image.

In accordance with another aspect, a computed tomography apparatus includes a rotatable gantry, a radiation emitter installed at one side of the gantry to emit radiation to an object, a filter installed in a radiation emission direction of the radiation emitter to pass or block radiation emitted from the radiation emitter, a cradle on which the object is placed, the cradle being moved into the gantry in a direction perpendicular to the gantry, and a radiation detector installed to the gantry at an opposite side of the radiation emitter and serving to receive radiation having passed through the object placed on the cradle and change the received radiation into an electric signal, wherein the filter passes radiation emitted from the radiation emitter in at least one irradiation position or irradiation zone during movement of the gantry, and blocks radiation emitted from the radiation emitter in at least one non-irradiation position or non-irradiation zone corresponding to the at least one irradiation position or irradiation zone.

The computed tomography apparatus may further include an image processor to read out a radiological image from the changed electric signal.

The image processor may generate a radiological image with respect to radiation blocked by the filter based on the generated radiological image. More specifically, the image processor may generate at least one intermediate radiological image between a plurality of radiological images acquired when emitting radiation plural times in the same direction.

The image processor may generate at least one radiological image captured in a direction opposite to a radiation emission direction based on the generated at least one intermediate radiological image.

The filter may include at least one opening to pass radiation, and the filter may rotate about a rotating shaft located inside or outside of the filter.

The filter may rotate at an angular speed corresponding to an angular speed of the gantry, and the angular speed of the filter may be determined based on the number of openings formed in the filter to pass radiation, the angular speed of the gantry, or the number of times radiation is emitted while the radiation emitter rotates once.

In accordance with a further aspect, a radiological image acquisition method using a computed tomography apparatus, includes acquiring image data in at least one irradiation position or zone by emitting radiation to an object when a radiation emitter reaches the irradiation position or zone, stopping radiation emission when the radiation emitter reaches at least one non-irradiation position or zone, and acquiring a plurality of image data in a plurality of irradiation positions or zones by repeating acquisition of the radiological image data and stop of the radiation emission, wherein the at least one irradiation position or zone and the at least one non-irradiation position or zone may be arranged to correspond to each other.

The radiological image acquisition method may further include calculating at least one image data captured in the non-irradiation zone based on at least one image data acquired in the at least one irradiation zone among the plurality of acquired image data.

The radiological image acquisition method may further include passing radiation emitted to the object through the filter if the radiation emitter reaches the at least one irradiation zone, and blocking radiation emitted to the object by the filter if the radiation emitter reaches the at least one non-irradiation zone, and the at least one irradiation zone may be located to correspond to the at least one non-irradiation zone.

In an exemplary embodiment, there is a radiation imaging apparatus including: a radiation emitter configured to emit radiation toward an object and to move around the object at a same time; a radiation detector configured to detect the radiation emitted from the radiation emitter, to change the detected radiation into a signal, and to store the signal; and an irradiation controller configured to control the radiation emitter so that the radiation is emitted toward the object in a first position around the object and such that no radiation is emitted toward the object in a second position corresponding to the first position.

In yet another exemplary embodiment, there is a radiation imaging apparatus including: a radiation emitter configured to move along a path about an object in a movement and to emit radiation toward the object during the movement; and a radiation detector configured to receive the radiation emitted from the radiation emitter and to change the received radiation into a signal, wherein the path about the object is divided into at least one irradiation zone in which the radiation emitter emits the radiation, and at least one non-irradiation zone in which the radiation emitter does not emit the radiation, and the at least one non-irradiation zone is located opposite to the at least one irradiation zone.

In one exemplary embodiment, there is a radiation imaging apparatus including: a radiation emitter configured to move along a first path about an object and to emit radiation toward the object; a filter disposed in a second path along which the radiation is emitted by the radiation emitter, to pass or to block the radiation emitted from the radiation emitter; and a radiation detector configured to receive the radiation emitted from the radiation emitter and to change the received radiation into a signal, wherein the filter passes the radiation emitted from the radiation emitter in at least one irradiation position or irradiation zone on the first path, and blocks the radiation emitted from the radiation emitter in at least one non-irradiation position or non-irradiation zone corresponding to the at least one irradiation position or irradiation zone.

In yet another exemplary embodiment, there is a radiological image acquisition method using a computed tomography apparatus, the method including: performing a radiation imaging operation to acquire a plurality of radiological image data in a plurality of directions by controlling a radiation emitter so that radiation is emitted toward an object in at least one direction around the object and so that no radiation is emitted toward the object in a direction corresponding to the at least one direction; and performing an image data combination operation to combine the plurality of radiological image data in the plurality of directions.

In one exemplary embodiment, there is a radiation imaging apparatus including: an emitter configured to simultaneously emit radiation toward an object and to move around the object; a detector configured to detect the radiation passing through the object, to convert the detected radiation into a signal, and to store the signal; and means for determining a location of the emitter or detector; a controller configured to control the radiation emitter based on the location of the emitter or detector detected by the means for determining, to emit the radiation toward the object when the location is at a first position and to not emit the radiation toward the object when the location is at a second position that is opposite to the first position.

In another exemplary embodiment, there is a radiation imaging apparatus including: an emitter configured to simultaneously emit radiation toward an object and to move around the object; means for shuttering the radiation emitted by the emitter; a detector configured to detect the radiation passing through the means for shuttering and the object, to convert the detected radiation into a signal, and to store the signal; and a controller configured to control the means for shuttering based on a location of the emitter or detector.

BRIEF DESCRIPTION OF THE DRAWINGS

These and/or other aspects will become apparent and more readily appreciated from the following description of the exemplary embodiments, taken in conjunction with the accompanying drawings of which:

FIGS. 3A, 3B, 3C, 3D, and 3E are views explaining radiation emission by the radiation emitter on a movement path according to an exemplary embodiment;

FIGS. 4A, 4B, and 4C are views explaining radiation emission by the radiation emitter on a movement path according to another exemplary embodiment;

FIG. 8 is a view explaining emission of radiation to an object according to an exemplary embodiment;

FIGS. 11A and 11B are views illustrating a configuration of an image processor according to several exemplary embodiments;

FIGS. 12D, 12E, and 12F are views respectively illustrating a spatial domain and a frequency domain acquired by the radiation imaging apparatus;

DETAILED DESCRIPTION

Figure 1:
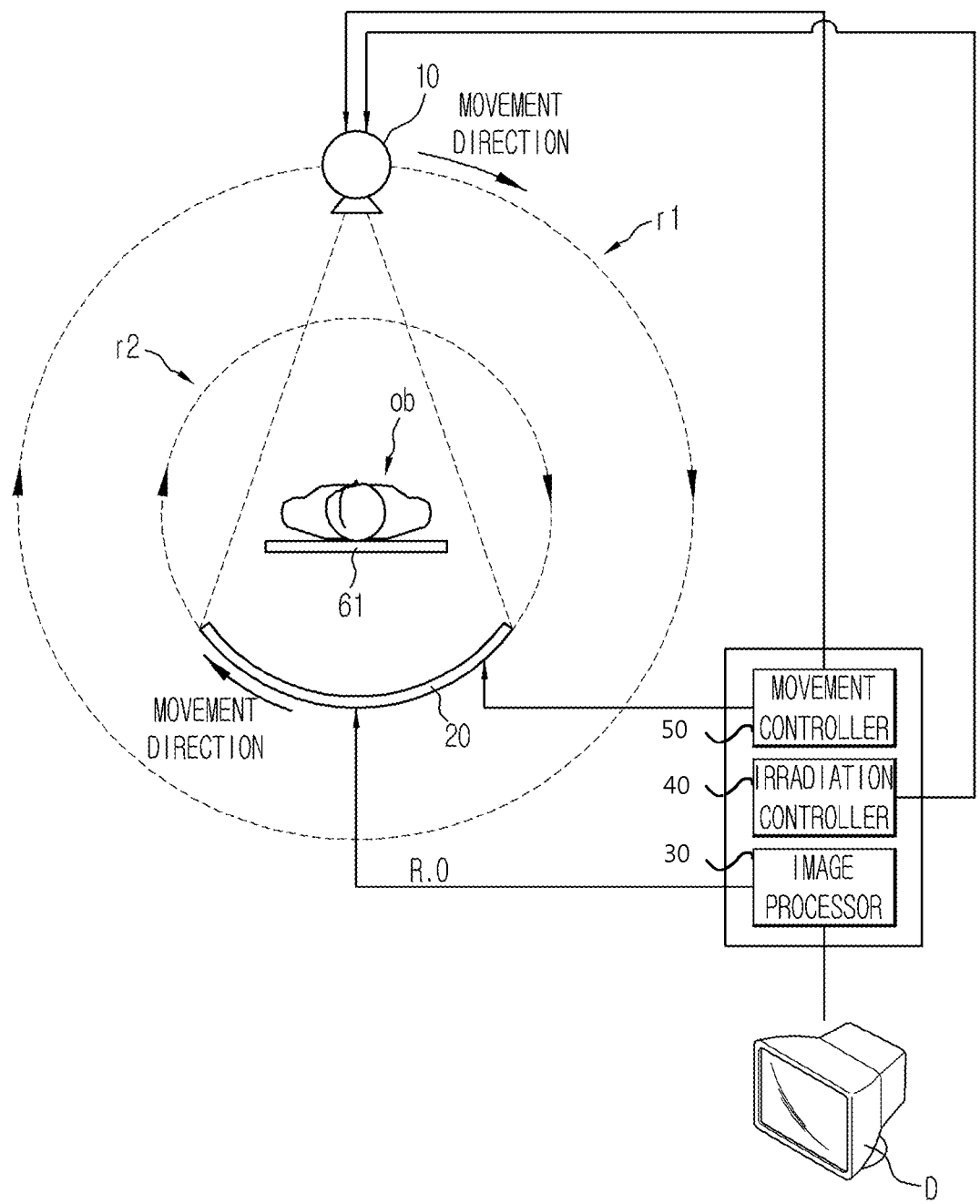
FIG. 1 is a view illustrating a whole configuration of a radiation imaging apparatus according to an exemplary embodiment.

Reference will now be made in detail to the exemplary embodiments, examples of which are illustrated in the accompanying drawings, wherein like reference numerals refer to like elements throughout.

FIG. 1 is a view illustrating a whole configuration of a radiation imaging apparatus according to an exemplary embodiment.

As illustrated in FIG. 1, according to the exemplary embodiment, the radiation imaging apparatus includes a radiation emitter 10 and a radiation detector 20. The radiation emitter 10 emits radiation, e.g., X-rays to an object ob. It is noted that the invention is not limited to the radiation emitter 10 which emits X-rays but also contemplates the use of other emitters which output emissions in the electromagnetic spectrum, other than X-rays. The radiation detector 20 receives radiation that has passed through the object ob or radiation directed to the vicinity of the object ob, and changes the received radiation into an electric signal for storage of the electric signal or into an electrical signal that is representative of radiation information or a radiological image which is subsequently stored.

The radiation imaging apparatus, as exemplarily illustrated in FIG. 1, may further include an image processor 30 that reads out a radiological image from the electric signal stored in the radiation detector 20. Alternatively, the image processor 30 reads out the radiation information or the radiological image stored in the radiation detector 20. The image processor 30 may process the generated radiological image, or may generate an additional radiological image using the generated radiological image.

The radiation imaging apparatus may further include an irradiation controller 40 to control whether or not to perform radiation emission by the radiation emitter 10, e.g., to control the emission of radiation by the radiation emitter 10. In one exemplary embodiment, the irradiation controller 40 controls the radiation emitter 10 to achieve such control.

Additionally, the radiation imaging apparatus may include a movement controller 50 to control movement of the radiation emitter 10, for example, rotational movement around the object ob. In another exemplary embodiment, the movement may be curved, arcuate, curvilinear, linear, or stepped. The movement controller 50 also controls movement of the radiation emitter 10 and the radiation detector 20. The movement of the radiation emitter 10 may correspond to the movement of the radiation detector 20. In one exemplary embodiment, the movement of the radiation emitter 10 may be matching, symmetric, synchronous, approximately matching, approximately symmetric, or approximately synchronous with respect to the movement of the radiation detector.

Functions of the image processor 30, the irradiation controller 40, and the movement controller 50 may be performed by a processor such as a Central Processing Unit (CPU) or a separate information processing device provided in the radiation imaging apparatus.

The radiation imaging apparatus may further include a cradle 61 on which the object ob is placed as illustrated in FIG. 1. The cradle 61 may be movable according to exemplary embodiments. In one embodiment, the cradle is a patient table.

Specifically, the radiation emitter 10 may emit radiation to the object ob while moving along a movement path r1 around the object ob. In this exemplary embodiment, the movement path r1, for example, may be an oval path or a circular path as exemplarily illustrated in FIG. 1. Although the movement path r1 may or may not be predetermined. In one example, the movement path r1 may be a part of a circle or oval, or may have an arc shape. As such, the radiation emitter 10 may emit radiation to the object ob while moving around the object ob along the circular, oval, or arc-shaped movement path r1 spaced apart from the object ob by a predetermined distance. However, the movement path r1 is not limited to circular or oval shapes, but may have other shapes, including those disclosed above.

The radiation emitter 10, according to exemplary embodiments, may emit radiation having different energy-bands to the object ob. This may enable acquisition of multi-energy X-ray (MEX) images.

The radiation detector 20 may move along a movement path r2 similar to the radiation emitter 10, so as to receive radiation emitted from the radiation emitter 10. Likewise, the movement path r2 may or may not be predetermined. In this case, the movement path r2 of the radiation detector 20 may have the same shape as the movement path of the radiation emitter 10. For example, as exemplarily illustrated in FIG. 1, the movement path r2 of the radiation detector 20 may be circular in the same manner as in the radiation emitter 10. In addition, the movement path r2 of the radiation detector 20 may have an oval shape, or may have an arc shape. The radiation detector 20 functions to detect radiation emitted from the radiation emitter 10 while moving along the circular, oval, or arc-shaped movement path r2 and to change the detected radiation into an electric signal to store the electric signal therein. However, the movement path r2 is not limited to circular or oval shapes, but may have other shapes, including those disclosed above.

According to an exemplary embodiment of the radiation imaging apparatus, the radiation emitter 10 and the radiation detector 20 may be movably installed to an external drive device, e.g., a gantry of a computed tomography apparatus. That is, the radiation emitter 10 and the radiation detector 20 may be circularly movable around the object ob in a predetermined direction via rotation of the gantry of the computed tomography apparatus. During movement around the object ob, the radiation emitter 10 and the radiation detector 20 may be arranged to face each other, to ensure appropriate reception of radiation. In this case, the radiation emitter 10 and the radiation detector 20 may have the same angular speed or angular acceleration, but are not necessarily limited thereto.

As described above, the movement controller 50 may be provided to move the radiation emitter 10 and the radiation detector 20.

Figure 2:
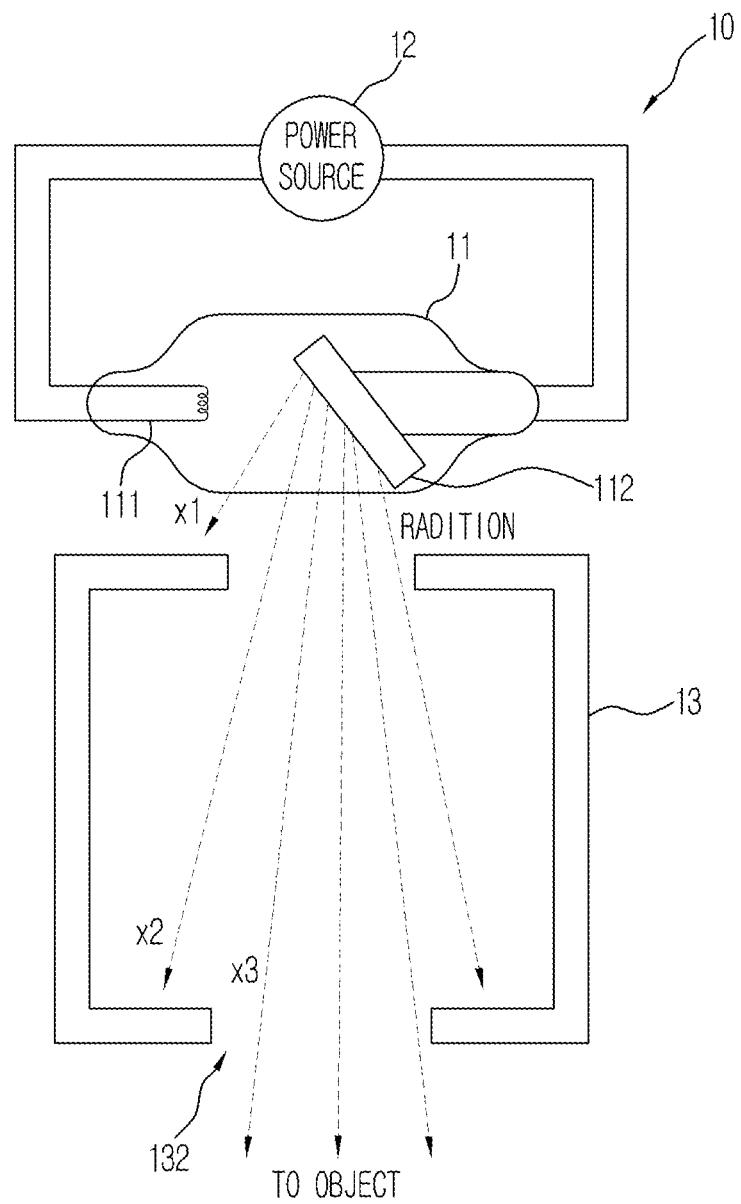
FIG. 2 is a view illustrating a radiation emitter according to an exemplary embodiment.

FIG. 2 is a view illustrating the radiation emitter 10 according to an exemplary embodiment.

As illustrated in FIG. 2, the radiation emitter 10 according to the exemplary embodiment may include a radiation tube 11 to generate radiation, e.g., X-rays, and a power source 12 electrically connected to the radiation tube 11 so as to apply a voltage to the radiation tube 11. Further, in other exemplary embodiments, the radiation emitter 10 may be an emitter which outputs other emissions in the electromagnetic spectrum other than X-rays.

A method of generating radiation by the radiation emitter 10 will now be described by way of example.

If the power source 12 of the radiation emitter 10 applies a predetermined voltage to the radiation tube 11, electrons are accelerated in a cathode filament 111 of the radiation tube 11 according to the voltage applied thereto to thereby move toward an anode 112. Upon reaching the anode 112, the accelerated electrons are rapidly reduced in speed near an atomic nucleus of the anode 112. In this case, radiation, e.g., X-rays are generated in the anode 112 according to the principle of energy conservation.

The radiation generated in the anode 112 is not essentially directed only in a direction and range that the user desires. Also, even if radiation is directed in a direction that the user desires, it may be necessary to reduce an emission range, for example, if an object is small or when it is desired to emit radiation to only a local part of an object. Therefore, to control a radiation emission direction and radiation emission range, for example, to control a wider or narrower emission range, according to an exemplary embodiment, a first collimator 13 may be installed on a radiation emission path from the radiation tube 11.

The collimator 13 assists the user in controlling a radiation emission direction and a radiation emission range by filtering and guiding a plurality of radiation into a particular direction and a predetermined range. The collimator 13 includes at least one collimator blade or collimator filter formed of a material capable of absorbing radiation, for example, lead (Pb).

In one example, as exemplarily illustrated in FIG. 2, some radiation x1 and x2 generated in the anode 112 and directed in a direction that the user does not desire are absorbed by, e.g., a partition 131 of the first collimator 130 so as not to be directed to the object ob, and radiation x3 directed in a direction that the user desires is directed toward the object ob through, e.g., an opening 132 of the first collimator 130.

In the case in which the radiation imaging apparatus is a computed tomography apparatus, the first collimator 130 may allow radiation generated by the radiation tube 11 to be directed in a fan shape or other shapes to the object ob.

The radiation emitter 10, as described above in FIG. 1, may emit radiation to the object ob while moving along a movement path around the object ob. In this case, the radiation emitter 10, according to an exemplary embodiment, may selectively emit radiation to the object ob for a period or according to a position on the movement path where the radiation emitter 10 is located. According to another exemplary embodiment, the radiation emitter 10 may continuously emit radiation to the object ob.

FIGS. 3A to 3E are views explaining radiation emission by the radiation emitter on a movement path according to an exemplary embodiment.

According to an exemplary embodiment of the radiation imaging apparatus, the radiation emitter 10 may emit radiation to the object ob only in a position or zone on a movement path thereof. The position or zone may or may not be predetermined. According to an exemplary embodiment, if the radiation emitter 10 emits radiation to the object ob in a position or zone as exemplarily illustrated in FIG. 3A, the radiation emitter 10 may not emit radiation to the object ob in a position or zone corresponding to the position or zone where the radiation emitter 10 emits radiation to the object ob. More specifically, the position or zone corresponding to the position or zone where radiation emission occurs may be a position or zone opposite to the position or zone about a point, an axis, or a point of reference, all of which may be predetermined or may not be predetermined. For example, the position or zone corresponding to the position or zone where radiation emission occurs may be a position or zone located in an opposite direction about the object ob. In addition, the position or zone corresponding to the position or zone where radiation emission occurs may be an opposite position or zone of the position or zone about the axis.

Figure 3A:
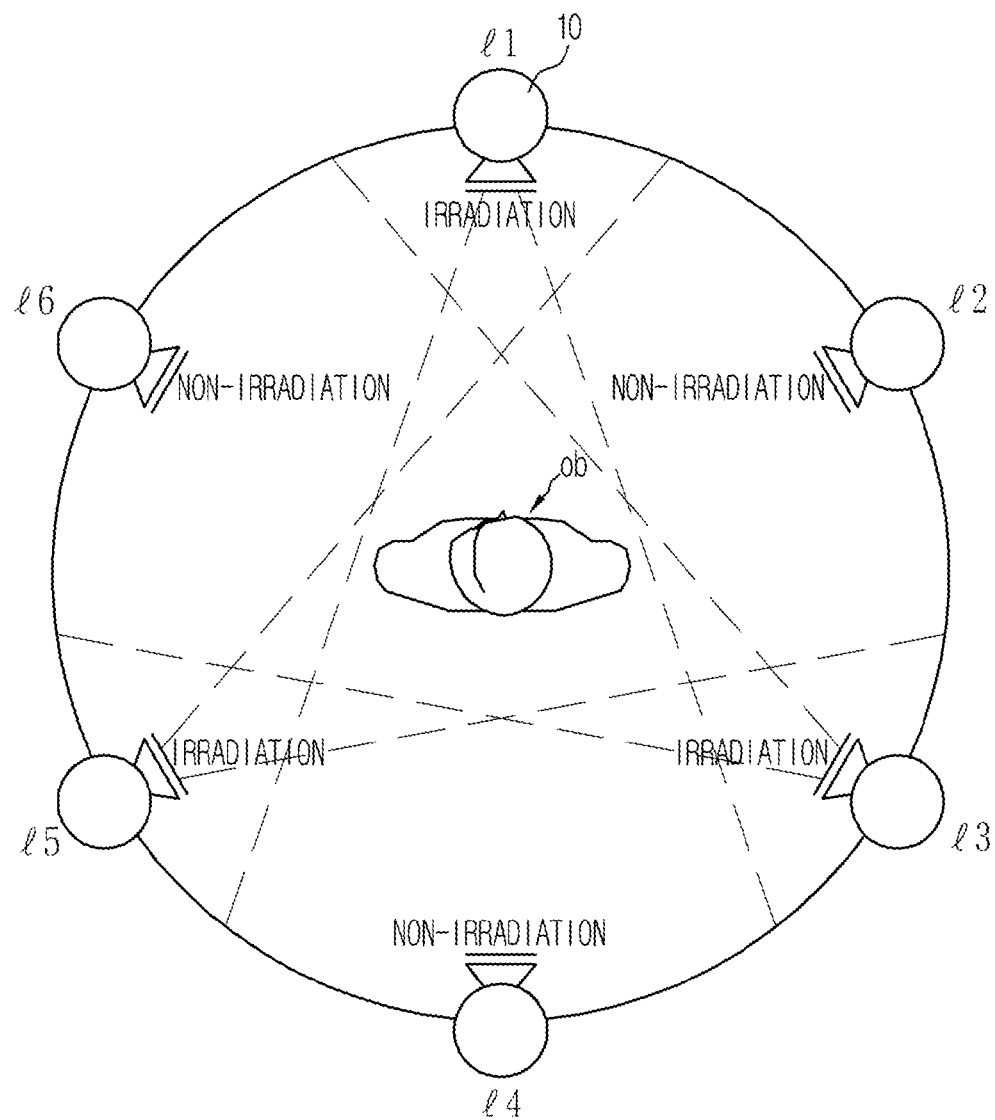

For example, as illustrated in FIG. 3A, the radiation emitter 10 may emit radiation to the object ob in positions on a movement path thereof, e.g., in a first position 11, a second position 13 and a fifth position 15, but may not emit radiation to the object ob in positions corresponding to the emission positions including the first position 11, the second position 13 and the fifth position 15, i.e. in a fourth position 14, a sixth position 16 and a second position 12. In other words, the object ob may be controlled so as not to receive radiation in a direction corresponding to a radiation emission direction, for example, in a direction opposite to the radiation emission direction if the radiation emitter 10 emits radiation to the object ob in at least one direction.

The radiation emitter 10, for example, as illustrated in FIG. 3B, may emit radiation to the object in irradiation zones a1, a3 and a5, but may not emit radiation to the object ob in non-irradiation zones a2, a4 and a6.

As illustrated in FIG. 3B, in the case in which a movement path of the radiation emitter 10 is a circular path defined around the object ob, the movement path may be divided into the irradiation zones a1, a3 and a5 and the non-irradiation zones a2, a4 and a6. The irradiation zones a1, a3 and a5 and the non-irradiation zones a2, a4 and a6 may be alternatingly arranged on the movement path so as not to be adjacent to the same zone. That is, the irradiation zones a1, a3 and a5 are respectively located at the left side of the respective non-irradiation zones a2, a4 and a6, and in turn the non-irradiation zones a2, a4 and a6 are respectively located at the left side of the respective irradiation zones a3, a5 and a1.

In this case, the respective non-irradiation zones a2, a4 and a6 and the respective irradiation zones a1, a3 and a5 are symmetrical to each other on the circular movement path as exemplarily illustrated in FIG. 3B. In other words, on the circular movement path, one non-irradiation zone a2, a4 or a6 may be present at an opposite side of one irradiation zone a1, a3 or a5.

According to one exemplary embodiment, the circular movement path may be equally divided. For example, as exemplarily illustrated in FIG. 3B, the movement path may be divided into six zones having the same size. In this case, each divided zone may be any one of the irradiation zones a1, a3 and a5 or any one of the non-irradiation zones a2, a4 and a6.

According to another exemplary embodiment, the circular movement path may be divided into zones of different sizes. Likewise, each divided zone may be any one of the irradiation zones a1, a3 and a5 or any one of the non-irradiation zones a2, a4 and a6. In this case, the non-irradiation zones a2, a4 and a6 corresponding to the irradiation zones a1, a3 and a5, or the irradiation zones a1, a3 and a5 corresponding to the non-irradiation zones a2, a4 and a6 may have the same size.

In the case in which the movement path is divided into a plurality of irradiation zones and non-irradiation zones, the radiation emitter 10 initiates emission of radiation to the object ob when entering the irradiation zones a1, a3 and a5 during movement along the movement path thereof. The radiation emitter 10 continuously emits radiation to the object ob in the irradiation zones a1, a3 and a5, and then stops radiation emission when entering the non-irradiation zones a2, a4 and a6 so as not to emit radiation to the object ob. As a result, radiation is not emitted to the object ob in the non-irradiation zones a2, a4 and a6.

To allow the radiation emitter 10 to perform radiation emission only in a position or zone, according to an exemplary embodiment, it may be possible for the radiation emitter 10 to selectively perform radiation emission based on positional information on the radiation emitter 10.

To acquire the positional information on the radiation emitter 10, according to one exemplary embodiment, an angular speed of the radiation emitter 10 may be used. That is, the radiation emitter 10, as illustrated in FIG. 1 or FIG. 3A, may be controlled to perform radiation emission based on an angular speed thereof during movement along a circular movement path thereof.

Through use of the angular speed of the radiation emitter 10, a position of the radiation emitter 10 after a predetermined duration has passed, i.e. a rotation angle of the radiation emitter 10 after having moved from a reference position may be acquired or calculated. The acquired rotation angle may be used to calculate the position of the radiation emitter 10, and whether or not to perform radiation emission by the radiation emitter 10 may be controlled based on the calculated position.

Additionally, according to another exemplary embodiment, to acquire positional information on the radiation emitter 10, a position sensor may be used.

To acquire positional information on the radiation emitter 10, an encoder or a detector may be placed on a movement path of the radiation emitter 10 or the radiation detector 20 to detect a position of the radiation emitter 10 or the radiation detector 20. In this case, to allow the encoder to detect a position of the radiation emitter 10 or the radiation detector 20, the radiation emitter 10 or the radiation detector 20 may be provided with a detection piece.

If the radiation imaging apparatus is a computed tomography apparatus, a detection piece may be formed at the gantry to which the radiation emitter 10 or the radiation detector 20 is installed, and an encoder, which is installed to a lateral portion of the gantry, may detect the detection piece on the gantry so as to detect a position of the radiation emitter 10 or the radiation detector 20.

In another exemplary embodiment, a combination of the angular speed and the detected location of the radiation emitter 10 or the radiation detector 20 may be used to determine the position of the same.

According to another exemplary embodiment, the radiation emitter 10 may selectively emit radiation to the object ob for a period or according to a pattern, whereby the period and the pattern may or may not be predetermined.

The radiation emission interval or pattern may be set or preset by the user. Of course, to set the radiation emission interval or pattern, the angular speed of the radiation emitter 10 may be used as described above.

By using an inverse number of the angular speed of the radiation emitter 10, a rotational-movement period of the radiation emitter 10 along a circular movement path may be calculated, and a radiation emission period, i.e. a period for which radiation is emitted and a period for which radiation is not emitted may be calculated based on the calculated period. For example, the radiation emission period may be acquired by dividing the calculated period by a 2× multiplied value of the number of times radiation is emitted. As such, radiation emission by the radiation emitter 10 may be performed according to the calculated radiation emission period.

To ensure that the radiation emitter 10 emits radiation to the object ob in a position or a zone on a movement path thereof, the radiation imaging apparatus, as illustrated in FIG. 1, may include the irradiation controller 40. The irradiation controller 40 may control radiation emission by the radiation emitter 10, allowing the radiation emitter 10 to selectively emit radiation to the object ob.

The irradiation controller 40, according to one exemplary embodiment, may acquire positional information on the radiation emitter 10, thereby controlling the radiation emitter 10 so as to selectively perform radiation emission according to the acquired positional information on the radiation emitter 10. In this case, as described above, the angular speed of the radiation emitter 10 may be used. Also, a separate position sensor may be used.

The irradiation controller 40, according to another exemplary embodiment, may control radiation emission by the radiation emitter 10 according to a period or pattern, both of which may be or may not be predetermined. That is, the irradiation controller 40 may allow the radiation emitter 10 to selectively perform radiation emission such that radiation is emitted only in the irradiation zones a1, a3 and a5 according to a period or pattern.

For example, the irradiation controller 40 may control the radiation emitter 10 to stop radiation emission when a emission duration has passed after radiation emission has begun, and to initiate radiation emission when a duration, i.e. a non-emission duration has passed after radiation emission has stopped.

Similar to the above description, the irradiation controller 40 may determine a radiation emission period using the angular speed of the radiation emitter 10, and control radiation emission based on the determined radiation emission period. Alternatively, the irradiation controller 40 may control radiation emission using a period or pattern input by the user.

In the exemplary embodiments, the control of the radiation emission may be based on temporal, spatial, or other factors. In other exemplary embodiments, calculation of the location of the radiation emitter 10 is not necessary and mere proximity of the radiation emitter 10 one of a number of elements would control the radiation emission. The elements would be selectively controlled in one of two states so that the proximity of radiation emitter 10 to an element in one state would turn on the emission of radiation and the proximity of the radiation emitter 10 to another element in another state would turn off the emission of radiation. The radiation emitter 10 would be in proximity to an element to be controlled by that element if the radiation emitter 10 is more closer to that element than other elements or is in contact with that element.

To control whether or not to perform radiation emission by the radiation emitter 10, the irradiation controller 40, specifically, may control the power source 12 of the radiation emitter 10 to allow the power source 12 to apply or not apply voltage to the radiation tube 11.

For example, the irradiation controller 40 may generate and transmit a control instruction to apply voltage to the radiation tube 11 upon determining that the radiation emitter 10 enters the irradiation zones a1, a3 and a5. Alternatively, the irradiation controller 40 may control application of voltage to the radiation tube 11 for a period such that radiation emission is performed only in the irradiation zones a1, a3 and a5.

Radiation is generated in the anode 112 of the radiation tube 11 according to a control instruction for voltage application or according to a voltage application period. The radiation emitter 10 emits radiation to the object ob only in the irradiation zones a1, a3 and a5.

Figure 3C:
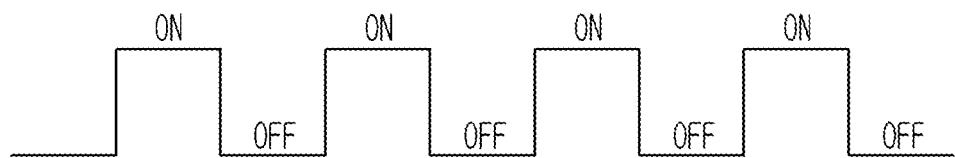

The state of the radiation emitter 10 or the voltage applied to the radiation tube 11 varies as illustrated in FIG. 3C. That is, the state of the radiation emitter 10 or the applied voltage has a pulsed shape. The state or voltage variation may be performed by the above-described irradiation controller 40.

For example, as illustrated in FIG. 3C, the irradiation controller 40 may transmit an emission instruction or emission-stop instruction to the radiation emitter 10, or may control radiation emission by the radiation emitter 10 on a per period basis, thereby allowing voltage to be applied (Power-On) or to not be applied (Power-Off) to the radiation emitter 10. Since the radiation emitter 10 emits radiation when voltage is applied thereto, radiation emission is performed in a Power-On state, and radiation emission stops in a Power-Off state.

The On/Off state change may be performed according to a control instruction of the irradiation controller 40 or a period as described above.

Results of substituting the On/Off state change for a circular movement path may be illustrated as in FIG. 3D. That is, as illustrated in FIG. 3D, the radiation emitter 10 emits radiation to the object ob in a Power-On state of the radiation emitter 10, and stops radiation emission in a Power-Off state, according to a control instruction or a period.

Figure 3E:
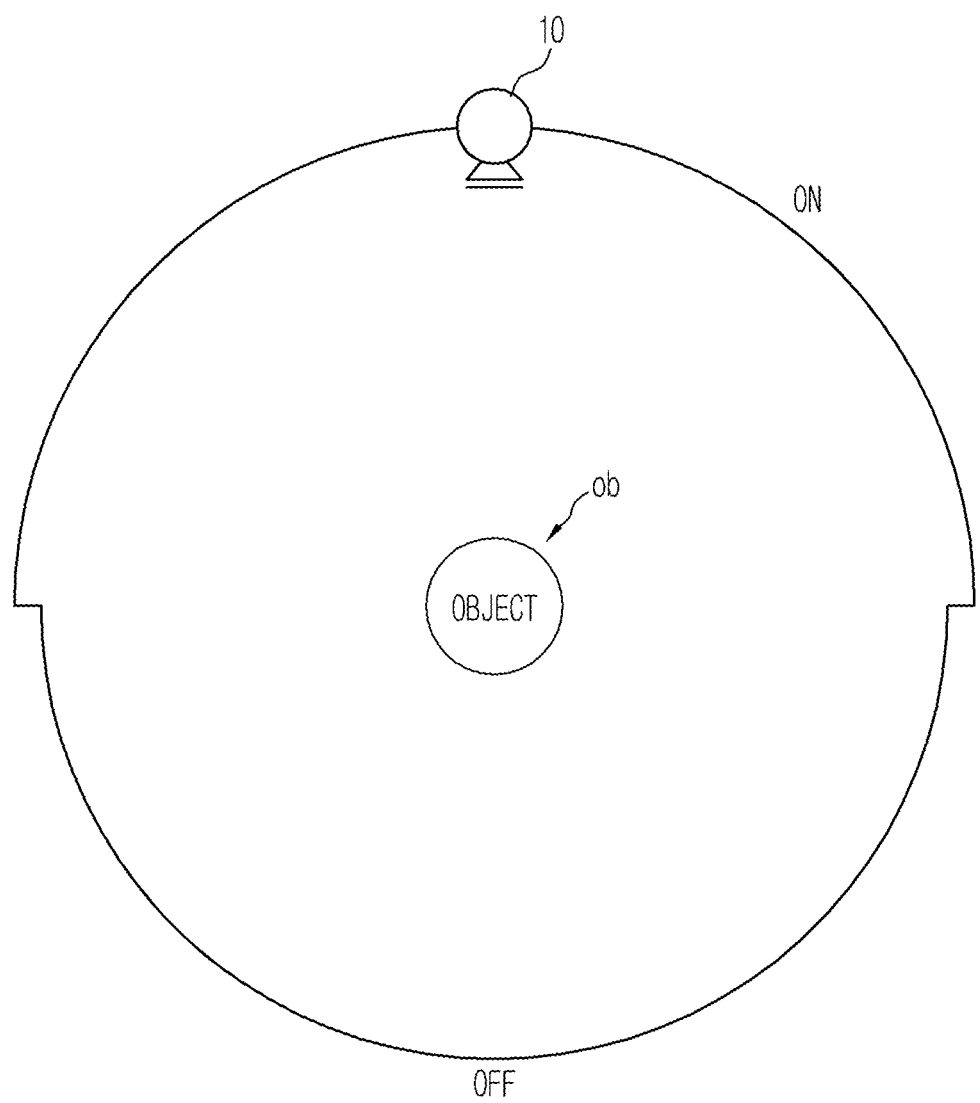

Although FIGS. 3A to 3D illustrate the case in which the movement path of the radiation emitter 10 is divided into three or more zones, the movement path may be divided into two equal zones as exemplarily illustrated in FIG. 3E. That is, as exemplarily illustrated in FIG. 3E, in the case of a circular movement path, the radiation emitter 10 emits radiation in one half the circular movement path, and does not emit radiation in the other half the circular movement path.

Figure 4A:
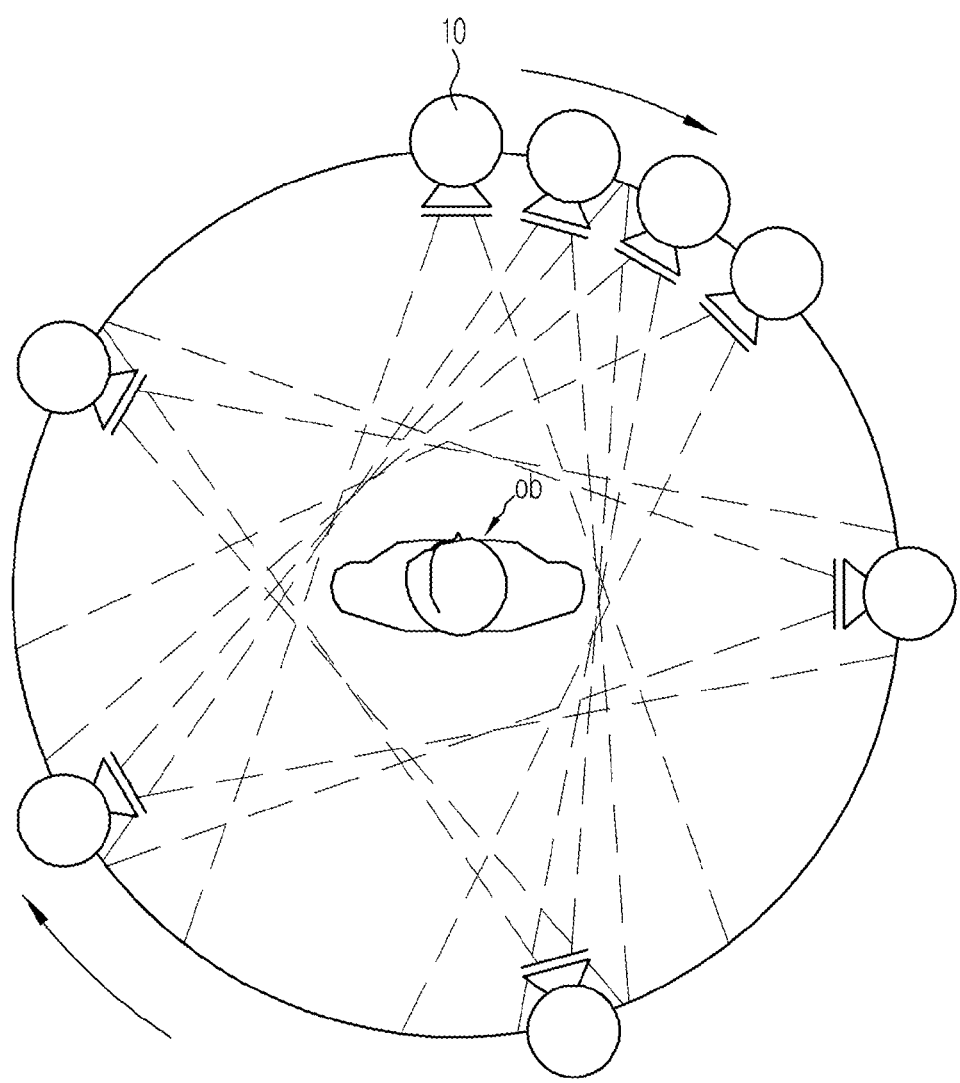
Figure 4C:
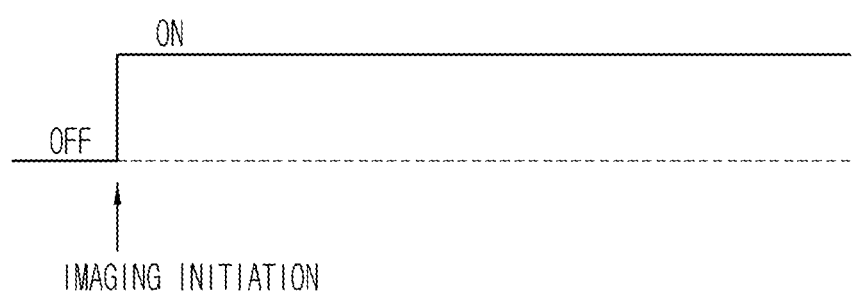

FIGS. 4A to 4C are views explaining radiation emission by the radiation emitter on a movement path according to another exemplary embodiment.

According to another exemplary embodiment of the radiation imaging apparatus, as exemplarily illustrated in FIG. 4A, the radiation emitter 10 may continuously generate and emit radiation toward the object ob. That is, the radiation emitter 10 may continuously emit radiation to the object ob, rather than selectively emitting radiation to the object via iterative On/Off state change as described above.

According to an exemplary embodiment of the radiation imaging apparatus, when the radiation emitter 10 continuously emits radiation, a filter 14 may be provided on a radiation emission path of the radiation emitter 10, i.e. in a direction through which the radiation is emitted.

The filter 14 may control emission of radiation to the object ob by passing or blocking radiation emitted from the radiation emitter 10 when the radiation emitter 10 is located in a position or zone.

Specifically, the filter 14 is configured to pass radiation emitted from the radiation emitter 10 when the radiation emitter 10 is located in a position (emission position) or zone (irradiation zone) while moving around the object ob. On the contrary, when the radiation emitter 10 is located in an opposite position (non-emission position) or zone (non-irradiation zone) about the object ob, the filter 14 blocks radiation emitted from the radiation emitter 10, thereby controlling emission of radiation to the object ob.

In the case in which the filter 14 is provided in a radiation emission direction from the radiation emitter 10, differently from the illustration of FIG. 3C, the radiation emitter 10 may continuously generate and emit radiation after imaging is initiated as illustrated in FIG. 4C. In other words, voltage is continuously applied to the radiation tube 11.

In an exemplary embodiment, the control of the filter 14 is in a manner that is the same or similar to the above-mentioned manner of controlling the emission of radiation by the radiation emitter 10.

FIGS. 5A to 5D are views illustrating an exemplary embodiment of the filter 14.

Figure 5A:
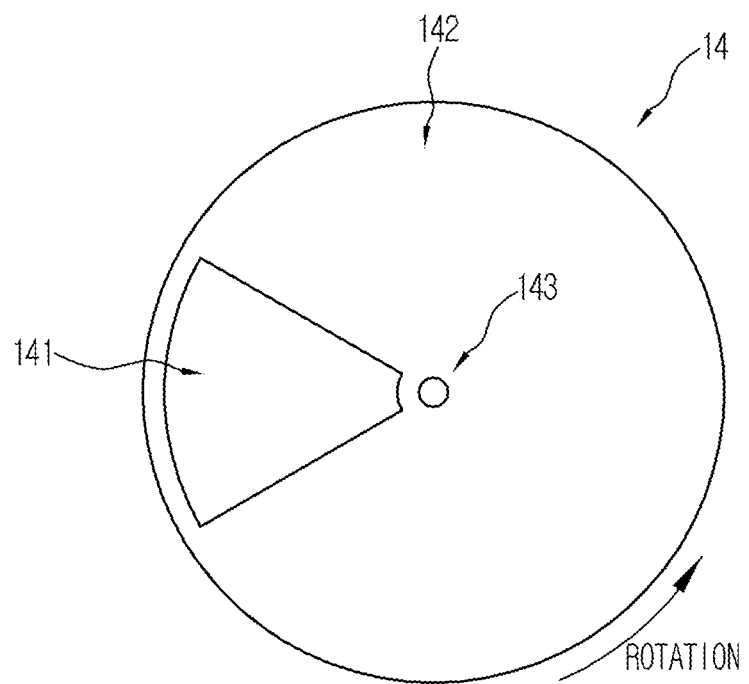
FIGS. 5A, 5B, 5C, and 5D are views illustrating an exemplary embodiment of a filter.
Figure 5B:
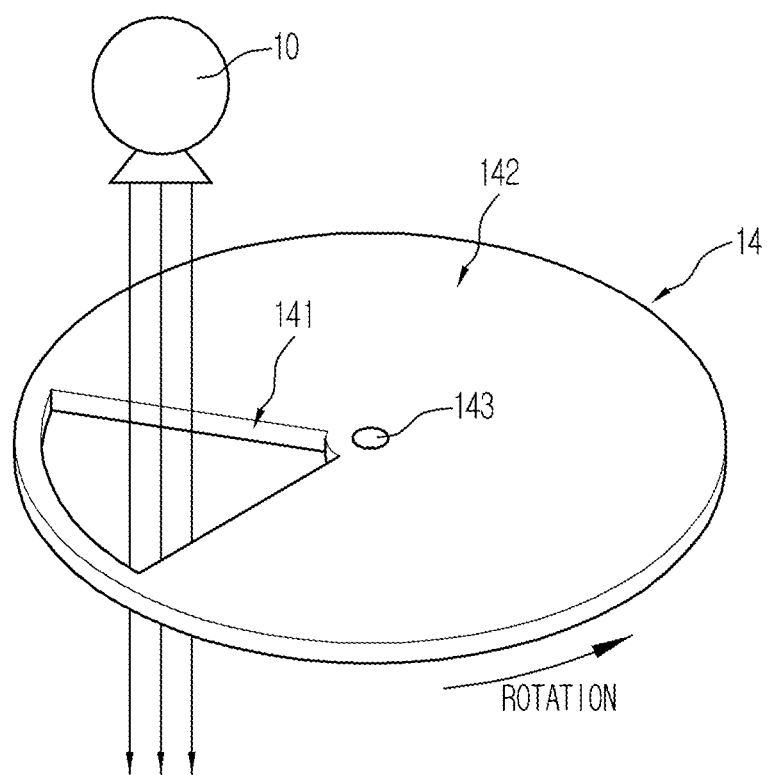
Figure 5C:
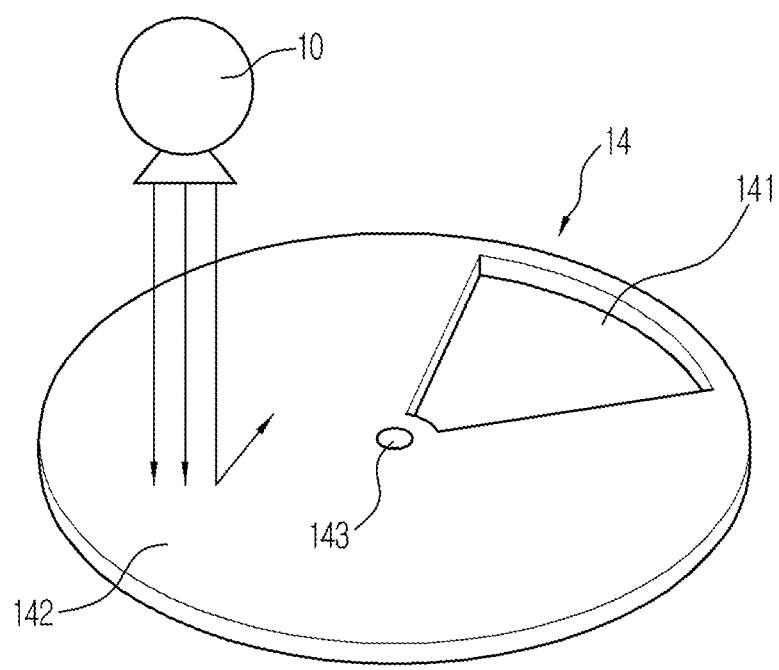

According to an exemplary embodiment, as illustrated in FIGS. 5A to 5C, the filter 14 has a disc shape, and an opening 141 for passage of radiation is formed in a portion of the disc. The opening 141 may have a semi-circular or fan shape according to exemplary embodiments. Additionally, to enable rotation of the disc-shaped filter 14, for example, a rotating shaft 143 may be provided at the center of the disc. The rotating shaft 143 may be located in another position on the disc except for the center position, and may be present around the disc.

The filter 14 passes or blocks radiation by rotating about the rotating shaft 143 in a radiation emission direction from the radiation emitter 10. When the opening 141 of the filter 14 is located in a radiation emission path of the radiation emitter 10 during rotation of the filter 14, as illustrated in FIG. 5B, the opening 141 passes the radiation.

Conversely, as illustrated in FIG. 5C, if another portion of the filter 14 rather than the opening 141, i.e. a radiation blocking portion 142 is located on the radiation emission path of the radiation emitter 10 during rotation of the filter 14, the radiation emitted from the radiation emitter 10 is blocked or absorbed by the filter 14. As such, the radiation emitted from the radiation emitter 10 is controlled by the filter 14 so as to be selectively emitted to the object ob.

Operation of the filter 14, for example, a movement speed of the filter 14, i.e. an angular speed of the filter 14 is set such that the object ob receives emission only within a zone, i.e. within the irradiation zone and does not receive radiation within the other zone, i.e. within the non-irradiation zone as illustrated in FIG. 3B.

Specifically, a rotational angular speed of the filter 14 may be adjusted according to a speed of the radiation emitter 10, for example, according to an angular speed of the radiation emitter 10 when the radiation emitter 10 moves along a circular movement path, according to the size and arrangement of the irradiation zones and non-irradiation zones, and according to the shape or size of the opening 141 of the filter 14.

Figure 5D:
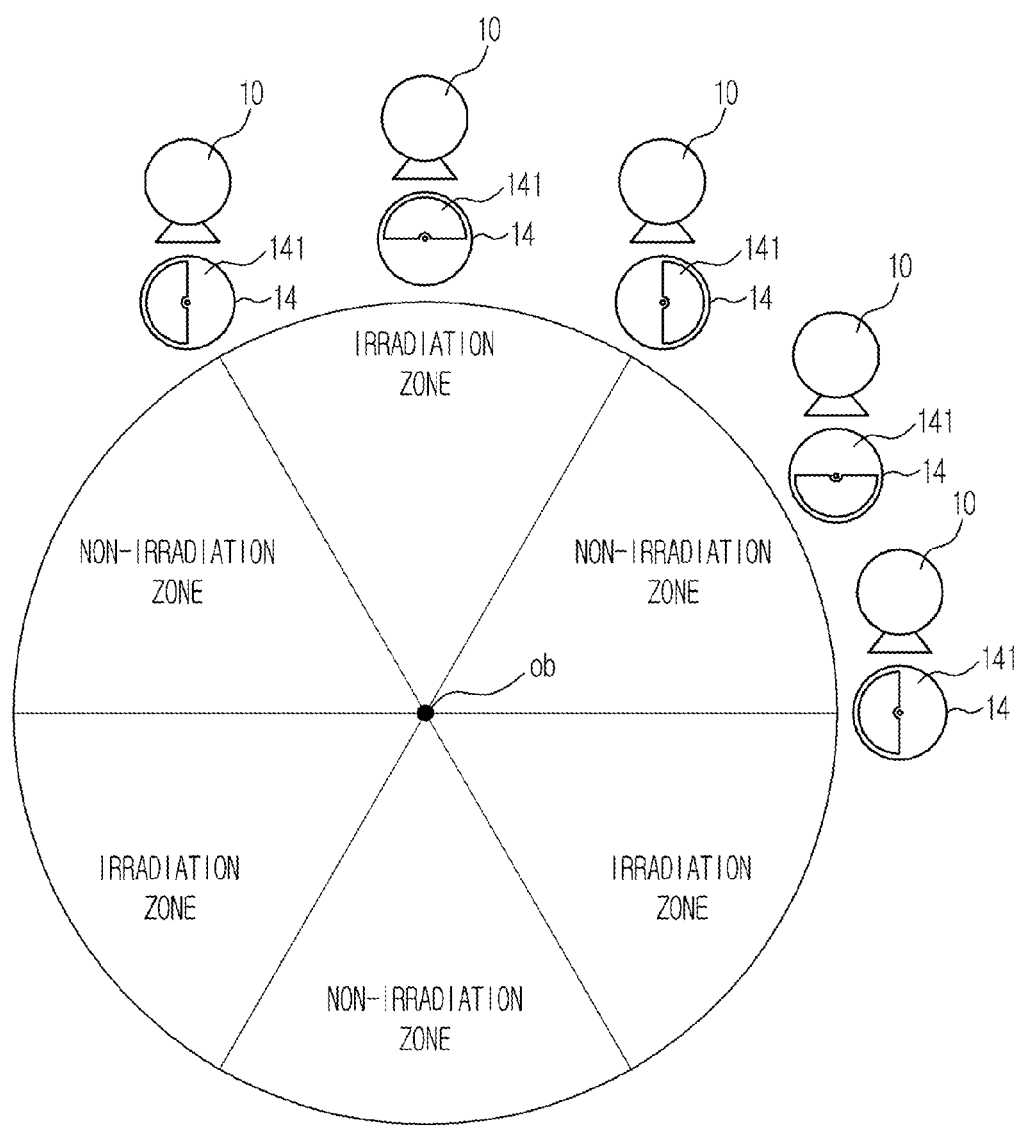

For example, assuming that there are six irradiation zones as illustrated in FIG. 5D and that the opening 141 occupies half of the filter 14 and the blocking portion 142 occupies the other half, a rotational angular speed of the filter 14 is set to three times an angular speed of the radiation emitter 10. That is, the rotational angular speed of the filter 14 is set as represented in the following Equation 1.

Rotational Angular speed of Filter $\omega_1$=Angular speed of Radiation emitter $\omega_2 \times 3$      Equation 1

That is, if the radiation emitter 10 moves along the circular movement path once, the filter 14 may rotate three times.

Once the rotational angular speed of the filter 14 has been set as described above, as illustrated in FIG. 5D, the opening 141 of the filter 14 is located on the radiation emission path of the radiation emitter 10 when the radiation emitter 10 enters an irradiation zone ((a) of FIG. 5D), thereby allowing radiation emitted from the radiation emitter 10 to reach the object ob. The radiation continuously reaches the object ob within the irradiation zone ((b) of FIG. 5D).

When the radiation emitter 10 enters the non-irradiation zone ((c) of FIG. 5D), the blocking portion 142 of the disc except for the opening 141 is located on the radiation emission path of the radiation emitter 10, thereby blocking radiation to prevent the radiation from reaching the object ob. The radiation is continuously blocked within the non-irradiation zone ((d) of FIG. 5D). Then, when the radiation emitter 10 again enters the irradiation zone, radiation reaches the object ob through the opening 141 ((e) of FIG. 5D).

As described above, the rotational angular speed of the filter 14 may be set based on the angular speed of the radiation emitter 10. When the angular speed of the radiation emitter 10 is changed, the rotational angular speed of the filter 14 is adjusted to correspond to the changed angular speed.

The rotational angular speed of the filter 14 may be adjusted according to the size or range of the irradiation zone or the non-irradiation zone. Although the rotational angular speed of the filter 14 may be kept constant, this may be changed as necessary.

For example, if the non-irradiation zone is longer than the irradiation zone, that is, if an arc length of the non-irradiation zone is longer than an arc length of the irradiation zone of FIG. 3B, the rotational angular speed of the filter 14 on the non-irradiation zone may be greater than the rotational angular speed of the filter 14 on the irradiation zone under control. Conversely, if an arc length of the non-irradiation zone is shorter than an arc length of the irradiation zone of FIG. 3B, the rotational angular speed of the filter 14 on the irradiation zone may be less than the rotational angular speed of the filter 14 on the non-irradiation zone under control.

The rotational angular speed of the filter 14 may be set based on the size of the opening 141 of the filter 14. For example, if the opening 141 of the filter 14 has about half the size of the disc as illustrated in FIG. 5D, the rotational angular speed of the filter 14 may be three times that of the angular speed of the radiation emitter 10 as described above.

Figure 6A:
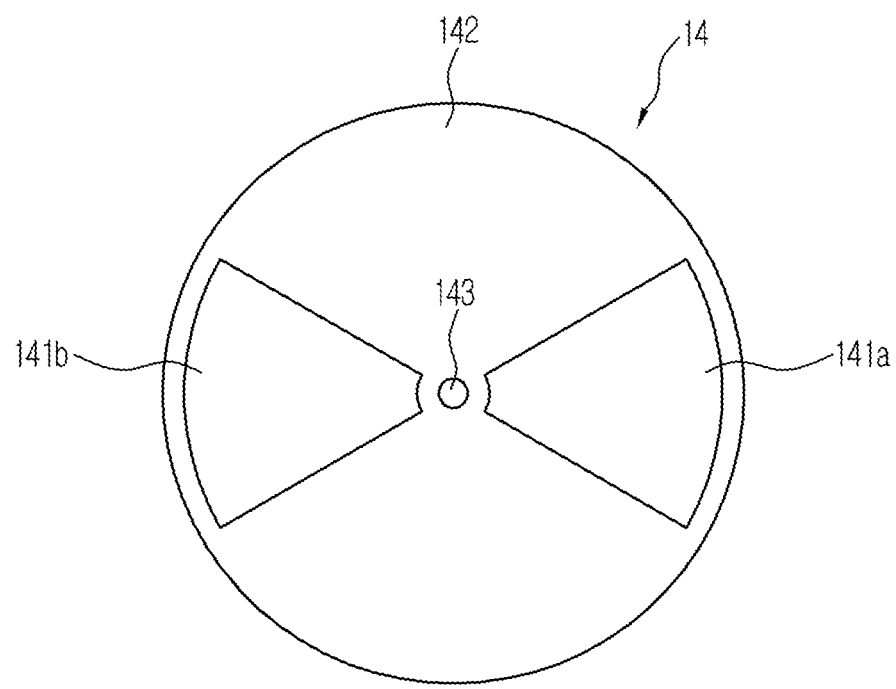
FIGS. 6A and 6B are views illustrating another exemplary embodiment of the filter.
Figure 6B:
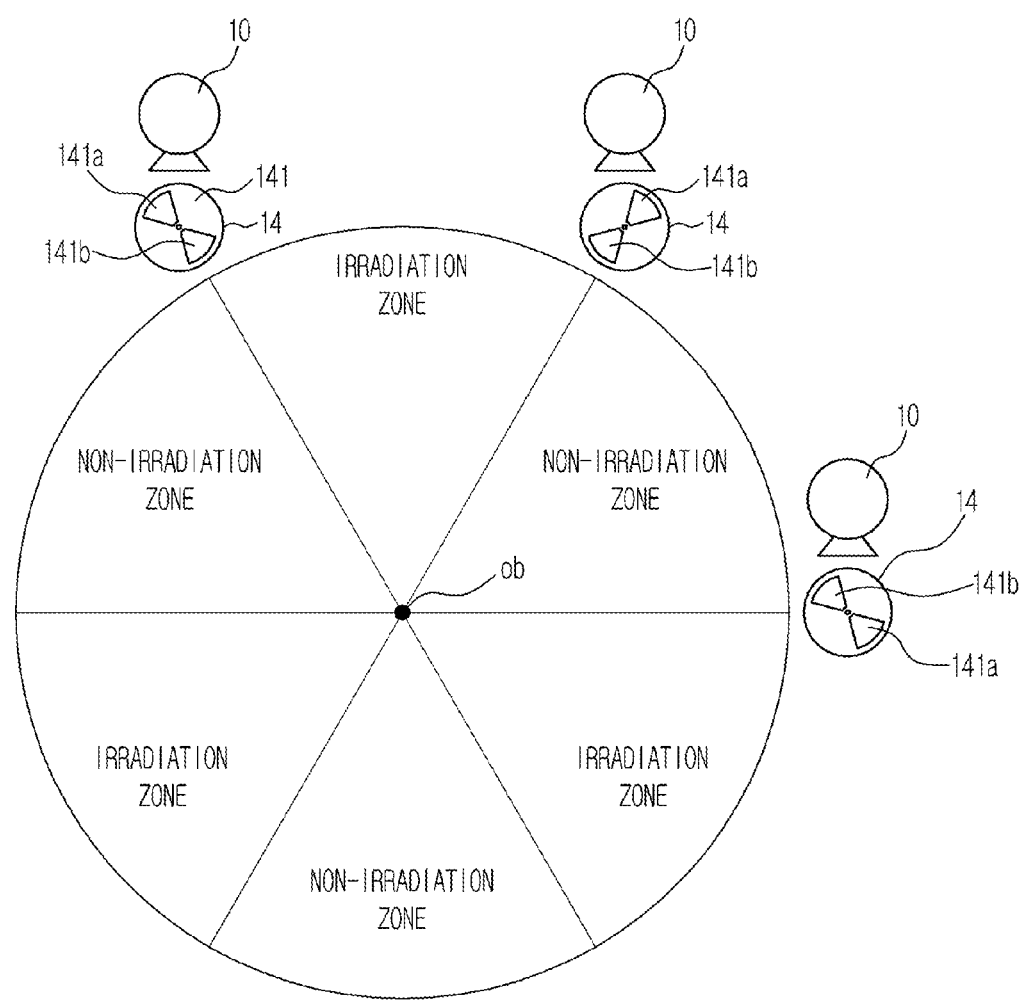

FIGS. 6A and 6B are views illustrating another exemplary embodiment of the filter.

As illustrated in FIG. 6A, the disc-shaped filter 14 may have a plurality of openings, for example, two openings 141a and 141b. In this case, the filter 14 may less rotate in proportion to the number of the openings 141a and 141b. Thus, the angular speed of the filter 14 may be reduced.

For example, as illustrated in FIG. 6A, it is assumed that there are two openings 141a and 141b of the filter 14 and the size of each opening is a quarter the size of the disc.

Then, as illustrated in FIG. 6B, if the radiation emitter 10 enters the irradiation zone, any one of the openings 141a and 141b of the filter 14 is located on the radiation emission path of the radiation emitter 10 to pass radiation. In this case, since the opening 141a is smaller than the opening 141 of the filter 14 as described above in FIG. 5D, it may be necessary to reduce the angular speed of the filter 14 under the assumption of the same size of the irradiation zone. That is, the filter 14 rotates by 180 degrees from a point (a) to a point (c) in the case of FIG. 5D, but rotates by 90 degrees from a point (f) to a point (g) in the case of FIG. 6B.

Starting from a point h where the filter 14 enters a next irradiation zone, the other opening 141b is located on the radiation emission path of the radiation emitter 10 to pass radiation.

As such, as illustrated in FIG. 6B, assuming that the filter 14 has the two openings 141a and 141b and the size of each opening is a quarter of the size of the disc, a rotational angular speed of the filter 14 is only 1.5 times an angular speed of the radiation emitter 10. That is, the filter 14 rotates by a half rotational angular speed of that in the exemplary embodiment illustrated in FIG. 5D.

For example, if the non-irradiation zone is longer than the irradiation zone, that is, if an arc length of the non-irradiation zone is longer than an arc length of the irradiation zone of FIG. 3B, the size of the opening 141 of the filter 14 may be less than the size of the blocking portion 142. In this case, as described above, the filter 14 may rotate by the same angular speed without requiring change in the angular speed of the filter 14.

Accordingly, the rotational speed of the filter 14 may be set based on the number, size, or shape of the openings 141 of the filter 14.

Figure 7A:
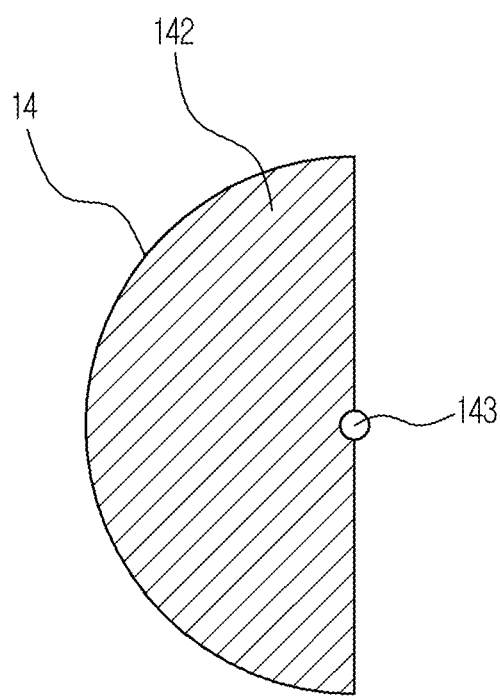
FIGS. 7A, 7B, and 7C are views illustrating various exemplary embodiments of the filter.
Figure 7B:
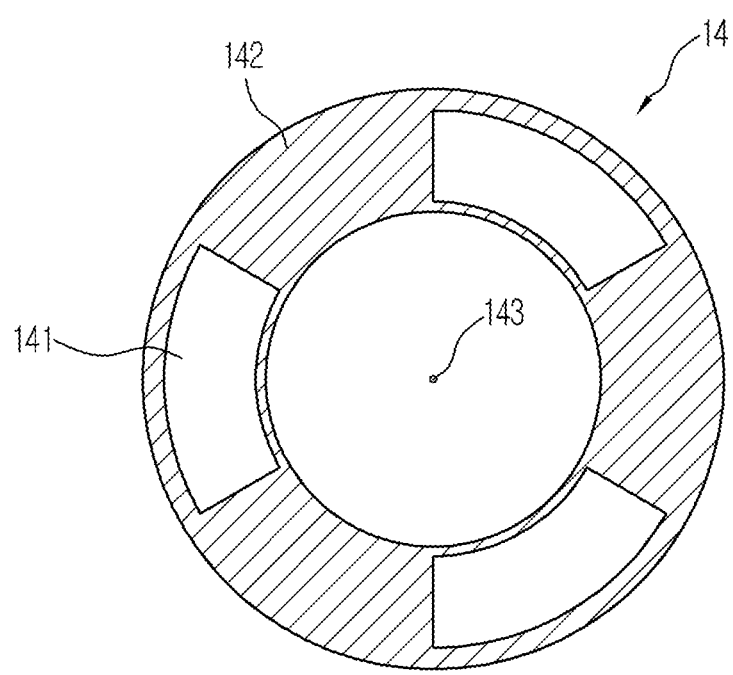
Figure 7C:
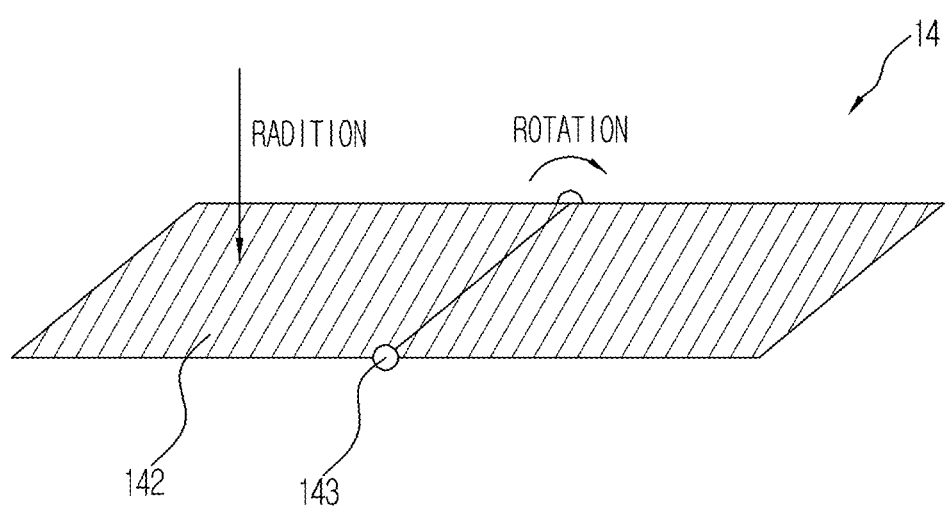

FIGS. 7A to 7C are views illustrating various exemplary embodiments of the filter 14.

As illustrated in FIG. 7A, the filter 14 may be a semi-circular plate such that the semi-circular blocking portion 142 blocks radiation. Similar to the above description, the filter 14 rotates about the rotating shaft 143.

As illustrated in FIG. 7B, the filter 14 may take the form of a combination of a plurality of fan-shaped blocking portions 142. In this case, the plurality of fan-shaped blocking portions 142 may be spaced apart from one another, such that a plurality of openings 141 for passage of radiation is present between the respective blocking portions 142. The plurality of openings 141 may also have a fan shape. Similar to the above description, the filter 14 including the plurality of fan-shaped blocking portions 142 may rotate about the rotating shaft 143.

As illustrated in FIG. 7C, at least one blade 142 may rotate about the rotating shaft 143 that is horizontal to the blade 142 to pass or block radiation.

In other exemplary embodiments, a filter may not have a completely rotative movement and may have back and forth motion, reciprocating motion, or oscillatory motion. For example, the filter 14 in FIG. 5A and any other filters would rotate or move back and forth within an arc that is less than 360 degrees, to act as a shutter in opening or closing a path through which the emitted radiation would pass.

As described above, the filter 14 may have various shapes, and an angular speed of the filter 14 may be set based on the shape of the filter 14.

As occasion demands, other shapes of the filter 14 to pass or block radiation may be applied to the radiation imaging apparatus.

According to an exemplary embodiment, the radiation imaging apparatus may further include the cradle 61 on which the object ob may be placed as illustrated in FIG. 1. The cradle 61 may take the form of a table on which a human body may be placed according to exemplary embodiments. If the radiation imaging apparatus is a computed tomography apparatus, the cradle 61 may move along a linear path.

If radiation is emitted to the object ob placed on the cradle 61, the radiation may be absorbed or reduced in transmittance by internal tissues or materials of the object ob according to properties of the internal tissues or materials of the object ob, for example, according to an attenuation coefficient of the internal materials. The radiation having passed through the object ob or having passed around the object ob rather than reaching the object ob is received by the radiation detector 20.

FIG. 8 is a view explaining emission of radiation to an object according to an exemplary embodiment.

As illustrated in FIG. 8, the object ob placed on the cradle 61 may not be exposed to radiation in a direction opposite to a radiation emission direction.

That is, as illustrated in FIG. 8, if radiation, for example, X-rays is directed to the object ob in a first direction, no radiation is directed to the object ob in an opposite direction, i.e. in a fourth direction. Similarly, if radiation is directed to the object ob in a third or fifth direction, no radiation is directed to the object in a direction opposite to the third or fifth direction, i.e. in a sixth or second direction.

In the case in which radiation is emitted to the object ob in a given direction, to ensure that no radiation is emitted to the object ob in a direction opposite to the given direction, it may be possible to control voltage to be applied to the radiation tube 11 of the radiation emitter 10 as described above, and to control passage of radiation using the filter 14 that is installed on a radiation emission path of the radiation emitter 10.

With the radiation imaging apparatus according to the exemplary embodiments, radiation is emitted to the object ob on the cradle 61 in a given direction, for example, in a first, third or fifth direction, and no radiation is emitted to the object ob in an opposite direction, for example, in a fourth, sixth, or second direction. Accordingly, the object ob is exposed to half as much radiation as compared to the case in which radiation is emitted to the object ob in all directions.

Figure 9:
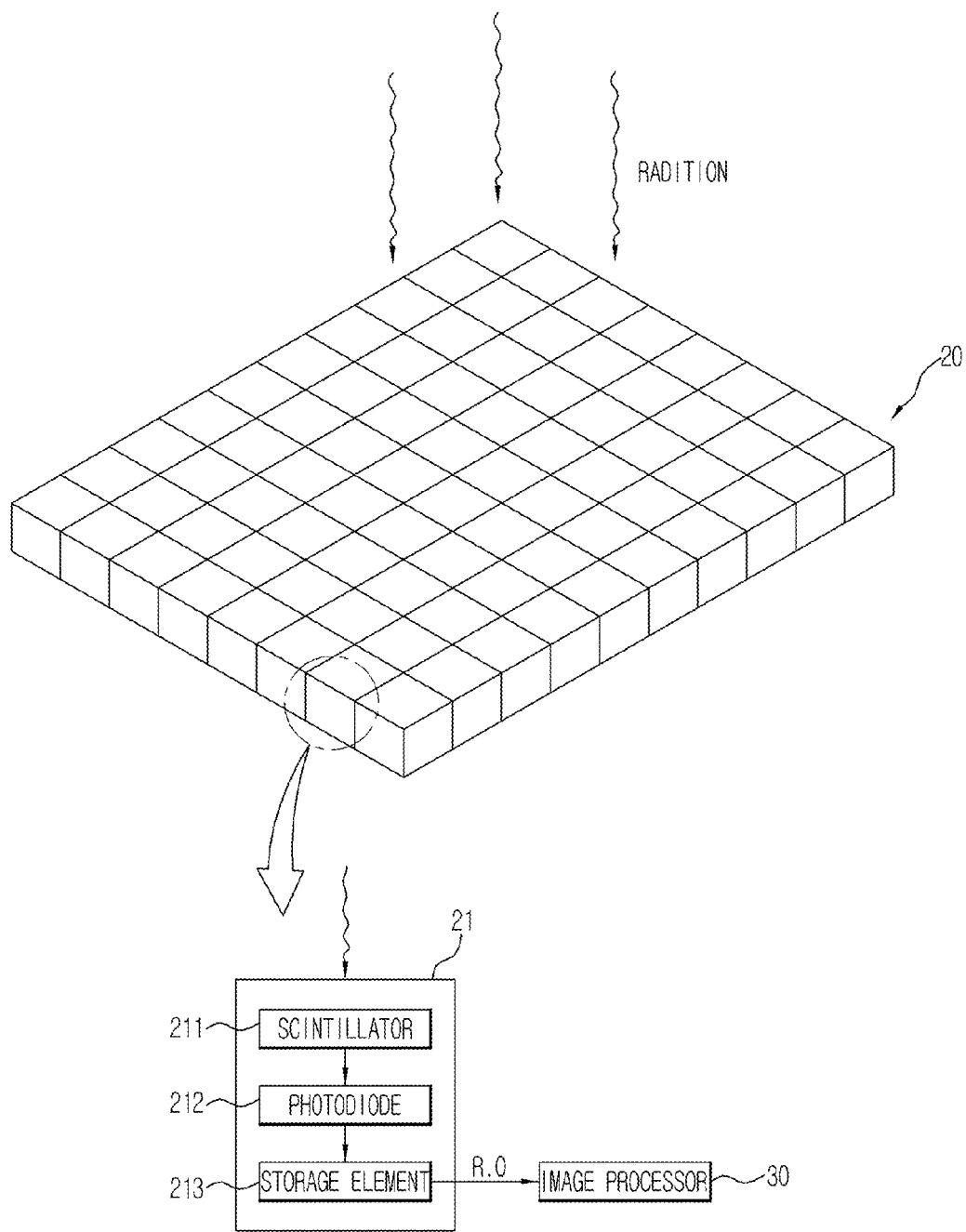
FIG. 9 is a view illustrating a radiation detector according to an exemplary embodiment.

FIG. 9 is a view illustrating the radiation detector 20 according to an exemplary embodiment.

The radiation detector 20, as illustrated in FIG. 9, may be divided into a plurality of pixels 21 to receive radiation. To receive radiation and change the radiation into an electric signal, each pixel 21 may include a light receiving element, such as a scintillator 211, a photodiode 212, and a storage element 213.

The scintillator 211 receives radiation and outputs photons, in particular, visible photons according to the received radiation. The photodiode 212 receives the photons output from the scintillator 211 and changes the photons into an electric signal. The storage element 213 is electrically connected to the photodiode 212 and stores the electric signal output from the photodiode 212. In one exemplary embodiment, the storage element stores the information represented by the electrical signal. Here, the storage element 213, for example, may be a capacitor. The electric signal stored in the storage element 213 of each pixel 21, as illustrated in FIGS. 1 and 9, is read out by the image processor 30. As the image processor 30 generates a radiological image based on the readout electric signal, the radiation detector 20 may acquire the radiological image corresponding to the received radiation.

After being subjected to desired image processing, the generated radiological image, as illustrated in FIG. 1, may be connected to the radiation imaging apparatus via a wireless or wired communication network, such as a cable, or may be displayed to the user via a display device D installed to the radiation imaging apparatus.

Figure 10A:
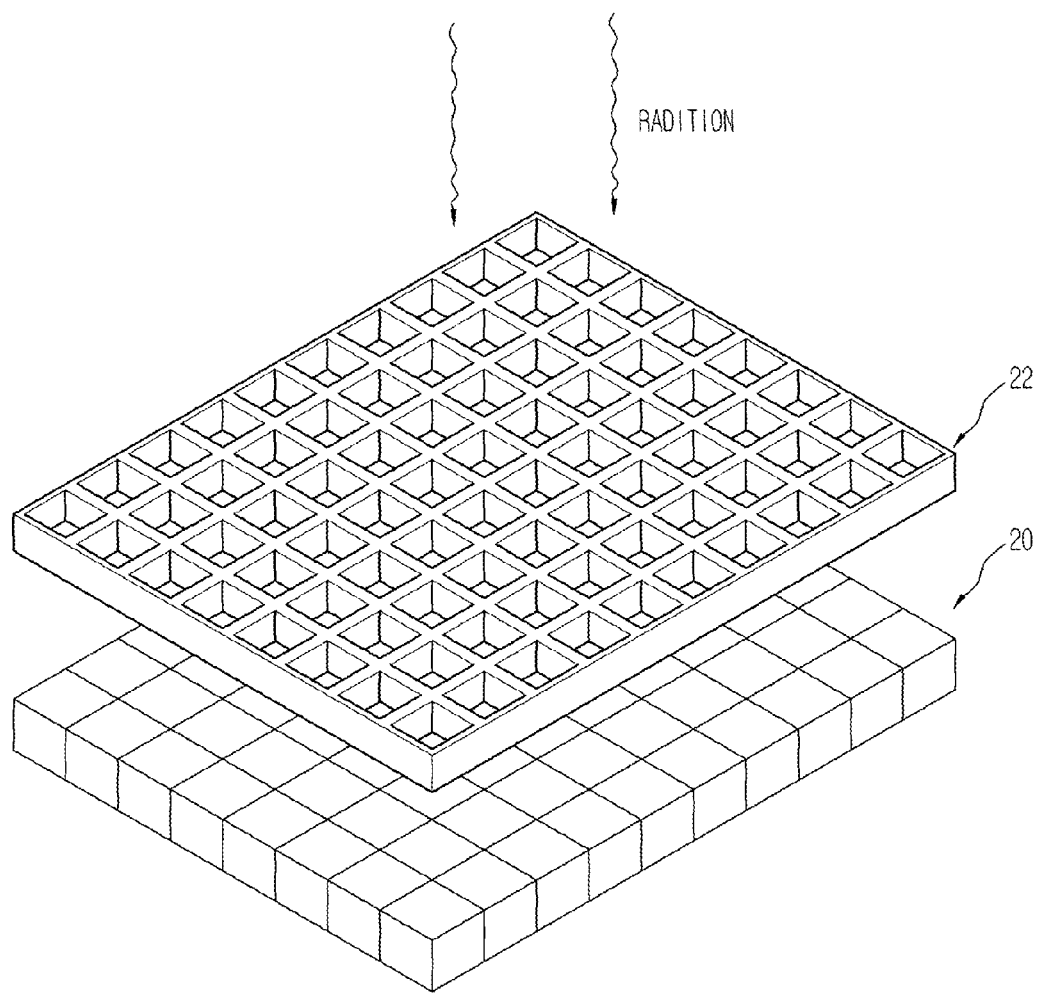
FIGS. 10A, 10B, and 10C are a perspective view and explanatory views of a collimator installed to the radiation detector.
Figure 10B:
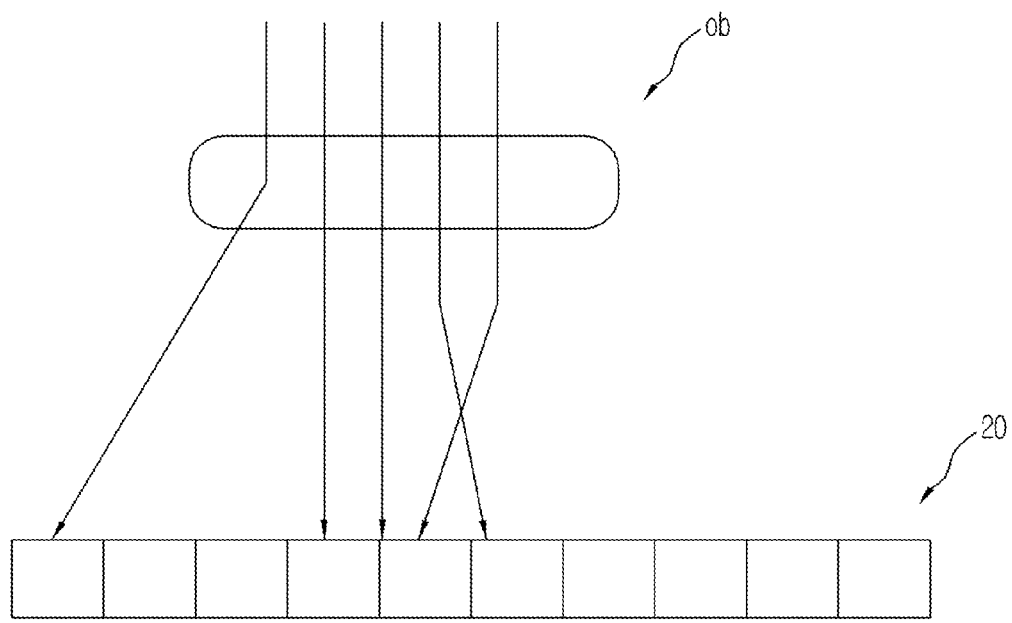
Figure 10C:
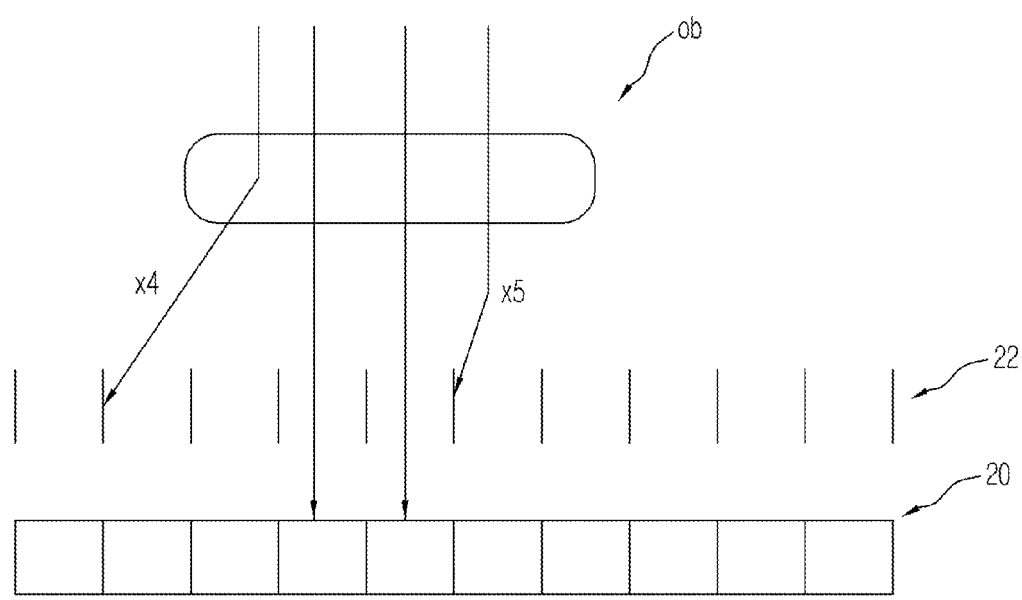

FIGS. 10A to 10C are a perspective view and explanatory views of a collimator installed to the radiation detector.

As illustrated in FIG. 10A, a second collimator 22 may be installed such that radiation having passed through the object reaches the second collimator 22 prior to reaching the radiation detector 20. The radiation may be scattered as designated by x4 and x5 of FIG. 10B while passing through the object ob. Scattering of radiation causes the pixels to receive incorrect positions of the scattered radiation, which may deteriorate accuracy of a finally generated radiological image.

The second collimator 22, as illustrated in FIG. 10C, absorbs the radiation scattered by the object ob and causes appropriate radiation to reach the radiation detector 20, which improves accuracy of an image.

Figure 11A:
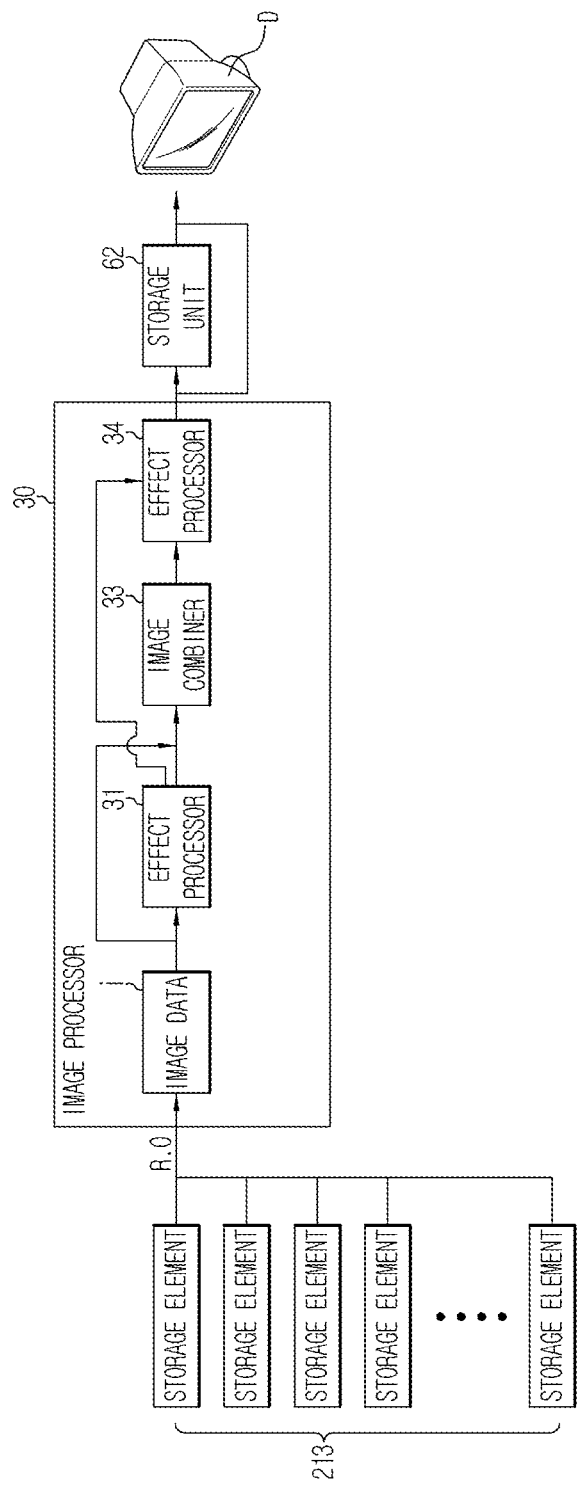

The radiation imaging apparatus may include the image processor 30 as illustrated in FIG. 1. FIGS. 11A and 11B are views illustrating a configuration of the image processor according to several exemplary embodiments.

As illustrated in FIG. 11A, the image processor 30 according to one exemplary embodiment may include an image generator 31, an image combiner 33, and an effect processor 34.

The image processor 30 simultaneously or sequentially reads out electric signals stored in the respective storage elements 213 of the pixels of the radiation detector 20, thereby acquiring raw image data i required for generation of a radiological image. The readout electric signals, i.e. raw image data i may be temporarily stored in a separate storage space.

The raw image data i is not changed from radiation emitted in all directions as described above with reference to FIGS. 3A to 8, but is changed from radiation emitted only at a position or zone, i.e. within an irradiation zone. That is, the raw image data I includes only image data in some of all directions, for example, in an irradiation zone, and does not include image data i' in the other directions, for example, in a non-irradiation zone.

If the storage elements 213 of the radiation detector 20 may temporarily store the electric signals transmitted from the photodiodes 212 whenever radiation is emitted or may do not store the electric signals repeatedly, i.e. if it may be necessary to delete previously stored electric signals from the storage elements 213 for storage of newly generated electric signals, the image processor 30 may read out the electric signals from the storage elements 213 whenever radiation is emitted. If the storage elements 213 of the radiation detector 20 may separately store the electric signals generated whenever radiation is emitted, it may not be essential for the image processor 30 to read out the electric signals whenever radiation is emitted.

The readout electric signals, i.e. raw image data i may be processed by the image generator 31 of the image processor 30.

The image generator 31 may generate a radiological image based on raw image data i. In this case, the image generator 31 may generate a radiological image such that pixels corresponding to the storage elements 213 in which respective electric signals are stored correspond to pixels constituting the radiological image.

If electric signals are read out from the storage elements 213 whenever radiation is emitted as described above, the image generator 31 may generate a radiological image whenever the electric signals are read out.

If the radiation emitter 10 emits radiation having different energy bands to the object ob, the image generator 31 may generate a plurality of radiological images corresponding to the different energy bands. By applying weighting to the respective radiological images or via combination or subtraction of the radiological images, a multi-energy radiological image may be generated.

The radiological image generated by the image generator 31 is not captured in all directions as described above in FIGS. 3A to 8, but is a radiological image captured when the radiation emitter 10 is located in a position or zone, i.e. in an irradiation zone.

Figure 12A:
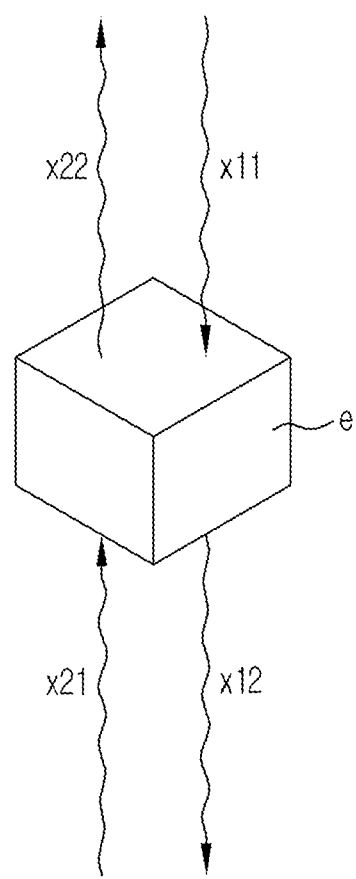
FIGS. 12A, 12B, and 12C are views respectively illustrating radiation emission in different directions and radiological images acquired by radiation emission.
Figure 12B:
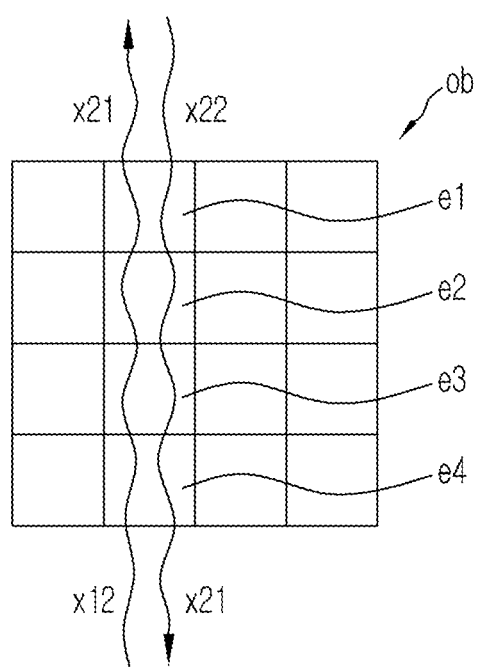
Figure 12C:
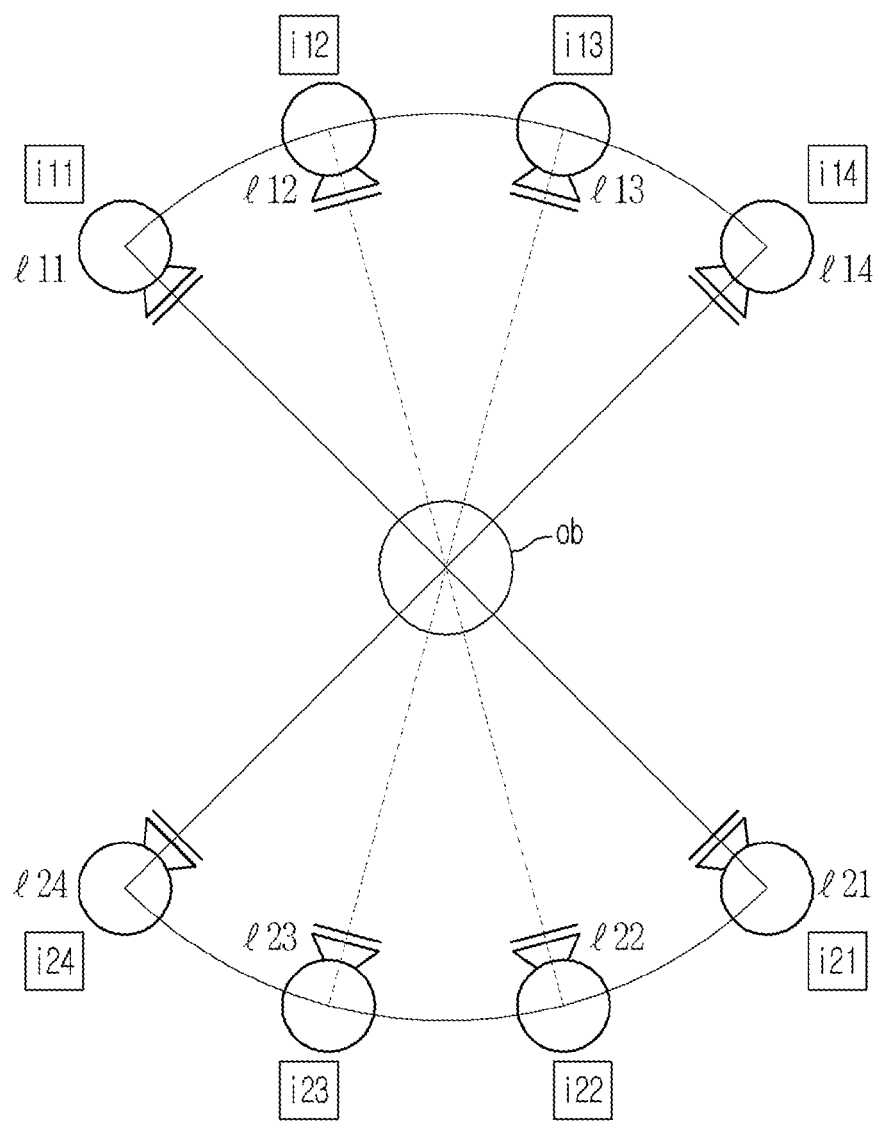

FIGS. 12A to 12C are views respectively illustrating radiation emission in different directions and radiological images acquired by radiation emission.

Referring to FIG. 12A, if radiation is emitted to a unit material e of the object ob, the radiation is attenuated while passing through the unit material e. More specifically, assuming that radiation x11 is emitted to the unit material e in a given direction, some of the radiation will be absorbed by the unit material e and some of the radiation will pass through the unit material e according to the constitution of the unit material e. As such, radiation x12 having passed through the unit material e is attenuated as compared to the radiation x11 by a rate. In this case, the attenuation rate is determined according to the kind or density of the material.

Likewise, if radiation x21 is emitted in a direction different from the above radiation emission direction, for example, in a direction opposite to the above radiation emission direction as exemplarily illustrated in FIG. 12A, radiation X22 having passed through the unit material e is attenuated by the rate depending on the unit material e. In this case, if the radiation x11 emitted in a given direction and the radiation x21 emitted in a different direction have the same magnitude, the radiation x12 and x22, which have been emitted in different directions and passed through the same unit material e, may have the same or very similar magnitude due to the same attenuation rate. In this way, if the radiation x11 and x21 having the same magnitude are emitted to the same unit material, the above-described radiation detector 20 acquires the same radiation x21 and x22.

Referring to FIG. 12B, the object ob may consist of a plurality of unit materials. In this case, the respective unit materials, for example, first to fifth unit materials e1 to e5 have the same properties, and thus radiation having passed through the respective unit materials e1 to e5 has the same attenuation rate. For example, as exemplarily illustrated in FIG. 12B, the radiation x12, which is acquired as the radiation x11 emitted to the object ob in a given direction passes through the plurality of unit materials e1 to e5, is equal to the radiation x22 which is acquired as the radiation x21 emitted in a direction corresponding to the given direction, for example, emitted in an opposite direction passes through the plurality of unit materials e1 to e5. In this way, the same image may be acquired using the radiation x11 and x21 emitted in different directions, for example, in opposite directions.

For example, as exemplarily illustrated in FIG. 12C, an eleventh radiological image i11, which is acquired by emitting radiation in a particular position, for example, in an eleventh position l11, may be equal to a twenty first radiological image, which is acquired by emitting radiation in a position corresponding to the particular position, for example, in a twenty first position l21. In this case, the particular position, i.e. the eleventh position l11 and the position, i.e. the twenty first position l21 corresponding to the particular position may be opposite to each other about the object ob.

Likewise, for example, twelfth to fourteenth radiological images i12 to i14, which are acquired by emitting radiation in twelfth to fourteenth positions l12 to l14, may be equal to twenty second to twenty fourth radiological images i22 to i24 which are acquired by emitting radiation in twenty second to twenty fourth positions corresponding to the twelfth to fourteenth positions l12 to l14.

Accordingly, even if radiation is not emitted in the twenty first to twenty fourth positions l21 to l24, radiological images of the object ob in all directions may be acquired using radiological images acquired by emitting radiation in the eleventh to fourteenth positions l11 to l14.

Consequently, as exemplarily illustrated in FIG. 3A or FIG. 4B, even when radiation is emitted to the object ob only in positions or zones, rather than being emitted to the object ob in all positions or zones, substantially the same radiological image as that acquired by emitting radiation to the object ob in all positions or zones may be acquired.

Accordingly, the image generator 31 of the image processor 30 may sufficiently acquire images of the object ob in all directions using only radiological images in particular positions or zones.

Figure 12D:
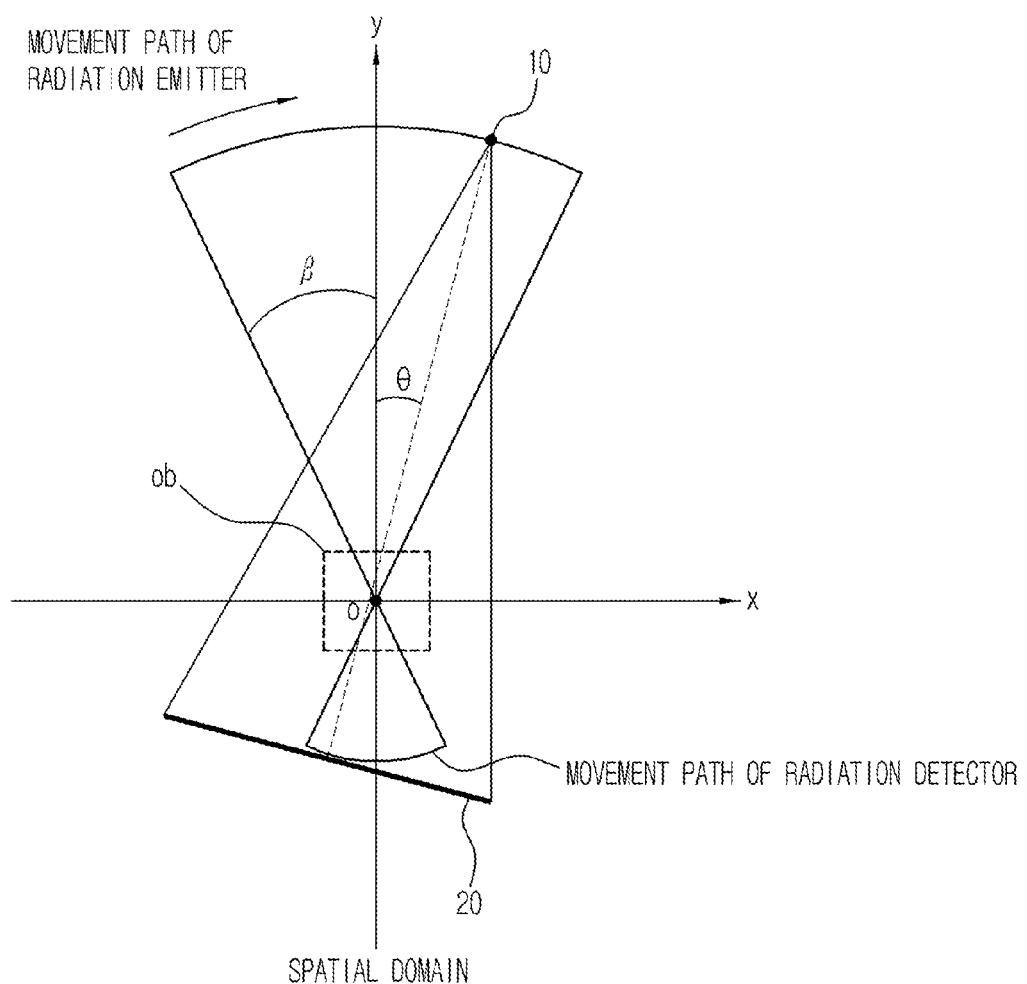
Figure 12E:
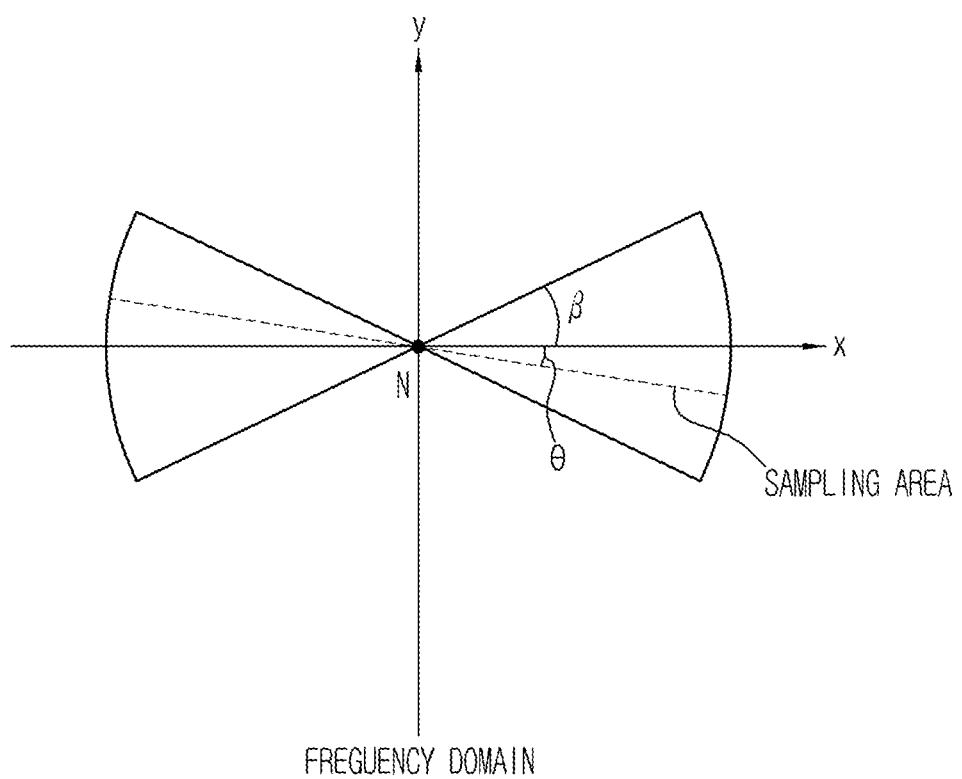

This will now be described in more detail with reference to FIGS. 12D to 12F. FIGS. 12D and 12E are views respectively illustrating a spatial domain and a frequency domain acquired by the radiation imaging apparatus.

A spatial domain depending on radiation emission from the radiation imaging apparatus, for example, a computed tomography apparatus is as illustrated in FIG. 12D.

In FIG. 12D, if the radiation emitter 10 emits radiation at a position θ, radiation having passed through the object ob reaches the radiation detector 20. The radiation emitter 10 and the radiation detector 20 move along respective movement paths thereof. In this case, the radiation emitter 10 emits radiation only within a range, i.e. within a range or an arc of −β to +β. That is, a relationship of −β≤θ≤+β is acquired. Through the above-described method, image data within a range for the object ob, i.e. within an X-ray irradiation zone may be acquired.

This may also be represented using a frequency domain as illustrated in FIG. 12E.

An image captured in the position θ of FIG. 12D may be represented by a dotted line (sampling area) within a fan of FIG. 12E. Since the radiation emitter 10 emits radiation only within a range, i.e. within a range of −β to +β, even in the case of a frequency domain, only data within a fan-shaped zone having a contained angle of 2β is acquired. In this case, as exemplarily illustrated in FIG. 12D, a plurality of symmetrical fan-shaped image data may be acquired from the frequency domain.

A relationship between a spatial domain and a frequency domain may be represented by the following Equations 2 to 4.

First, data acquired by emitting radiation in a given direction in the spatial domain may be defined by the following Equation 2.

$$P_\theta(t) = \iint f(x,y)\delta(x\cos\theta + y\sin\theta - t)dxdy \qquad \text{Equation 2}$$

Here, $P_\theta(t)$ is acquired radiation emission data, and x and y are coordinates of an arbitrary unit material within the object. In addition, f(x, y) is data on the arbitrary unit material at the coordinates (x, y) within the object. θ is a contained angle between an emission direction and the X-axis.

The above Equation 2 may be represented as the first line of the following Equation 3, and the following Equation 4 may be acquired via calculation of Equation 2 and Equation 3.

$$P_\theta(\omega) = \int P_\theta(t)e^{-j2\pi\omega t}dt \qquad \text{Equation 3}$$
$$= \iint f(t\cos\theta - l\sin\theta, t\sin\theta + l\cos\theta)e^{-j2\pi\omega t}dtdl$$
$$= \iint f(x,y)e^{-j2\pi\omega(x\cos\theta + y\sin\theta)}dxdy$$

$$P_\theta(\omega) = F(\omega\cos\theta, \omega\sin\theta) \qquad \text{Equation 4}$$

The above Equation 4 corresponds to the above-described frequency domain. Accordingly, the spatial domain depending on emission of radiation by the radiation emitter as exemplarily illustrated in FIG. 12D may be represented as the frequency domain as exemplarily illustrated in FIG. 12E.

Meanwhile, if radiation is emitted to the object ob only in a particular zone as exemplarily illustrated in FIG. 3A or FIG. 4B, data is acquired in the frequency domain as exemplarily illustrated in FIG. 12F. That is, for example, if radiation is emitted in a first irradiation zone a1 of FIG. 3B, data 1 may be acquired as exemplarily illustrated in (a) of FIG. 12F. Subsequently, if radiation is emitted in a second irradiation zone a3, novel data 2 may be acquired as exemplarily illustrated in (b) of FIG. 12F. Likewise, if radiation is emitted in a third irradiation zone a5, novel data 3 may be additionally acquired as exemplarily illustrated in (c) of FIG. 12F. Consequently, image data in the entire region may be acquired as exemplarily illustrated in (c) of FIG. 12F.

As described above, the radiation imaging apparatus does not emit radiation to the object ob in a direction corresponding to a particular radiation emission direction, for example, in a direction opposite to the particular direction, i.e. within a non-irradiation zone, and therefore the radiation detector 20 does not detect any radiation. Accordingly, no image data is acquired in the non-irradiation zone.

Accordingly, by emitting radiation to the object ob only in some directions, it may be possible to acquire the same image or substantially the same image as that acquired when emitting radiation in all directions while reducing radiation exposure of the object ob.

Meanwhile, the image combiner 33 may generate a new radiological image by combining acquired radiological images or image data on the radiological images.

More specifically, the image combiner 33 may generate a successive radiological image, for example, a panorama image or moving image by connecting or combining radiological images generated by the image generator 31.

The effect processor 34 performs desired image processing on a radiological image i1 generated by the image generator 31 or a radiological image generated by the image combiner 33, thereby improving the quality and readout efficiency of a radiological image to be displayed on the display device D. Here, desired image processing may include, for example, post-processing including adjustment of color, brightness, contrast, or clarity of all or some of the generated radiological images as well as removal of noise. The effect processor 34 may perform the desired image processing on the generated radiological image in response to user requests or based on predefined setting.

FIG. 11B is a view illustrating a configuration of the image processor according to another exemplary embodiment.

The image processor 30 of the present exemplary embodiment may further include a reverse image generator 32.

The reverse image generator 32 may generate, using a radiological image captured in a particular direction, for example, a radiological image captured in an irradiation zone, a radiological image captured in a direction corresponding to the particular direction, for example, in a direction opposite to the particular direction, for example, in a non-irradiation zone. Alternatively, the reverse image generator 32 may calculate image data i' related to an image captured in a direction corresponding to a particular direction, thereby compensating for insufficient image data for a radiological image, for example, a tomographic image.

The reverse image generator 32 may generate and calculate, using the radiological image generated based on radiation emitted in the particular direction or using the acquired image data I, an image in a direction corresponding to the particular direction, for example, in a direction opposite to the particular direction or image data i' in a direction corresponding to the particular direction.

For example, the reverse image generator 32 may acquire a reverse image by rearranging each data of a radiological image generated based on radiation emitted in a particular direction at a symmetrical position about a center line perpendicular to the particular direction.

According to exemplary embodiments, the reverse image generator 32 may generate a reverse image or reverse image data i' by applying weighting to a part of a radiological image or image data i captured in a particular direction.

Additionally, the reverse image generator 32 may generate or calculate a single reverse image or reverse image data i' by generating or calculating new radiological images or image data based on a plurality of radiological images or image data i captured in a plurality of directions, and thereafter combining the acquired radiological images or image data. In this case, at least one reverse image may be acquired by combining the plurality of radiological images, or by applying weighting to each of the plurality of radiological images, combining the resulting radiological images, and calculating a reverse image of the combined image.

In this case, the image combiner 33 may generate a successive radiological image, for example, a panorama image or moving image by connecting or combining radiological images generated by the image generator 31 and the reverse image generator 32.

The image combiner 33 may combine image data i of at least one irradiation zone acquired from the storage elements 213 with reverse image data i of at least one non-irradiation zone calculated by the reverse image generator 32, thereby generating a radiological tomographic image for the cross section of the object ob to which radiation is emitted.

The image generated by the image processor 30, as exemplarily illustrated in FIG. 11A, may be transmitted to a storage unit 62 or the display device D.

The storage unit 62, as exemplarily illustrated in FIG. 11, temporarily or semi-permanently stores a radiological image in a particular direction and a radiological image in a direction opposite to the particular direction generated by the image processor 30, an image generated by the image combiner 33 via combination of the above radiological images, or a radiological image generated by performing desired post-processing on the above radiological images.

The display device D displays a radiological image generated by the image processor 30 or stored in the storage unit 62 to a user, for example, a doctor, nurse, radiologist, or patient. In an exemplary embodiment, the display device D may be a monitor mounted to the radiation imaging apparatus, an external monitor connected to the radiation imaging apparatus via a wired or wireless network, or an information processing device, such as a computer, to which a monitor is connected.

Figure 13:
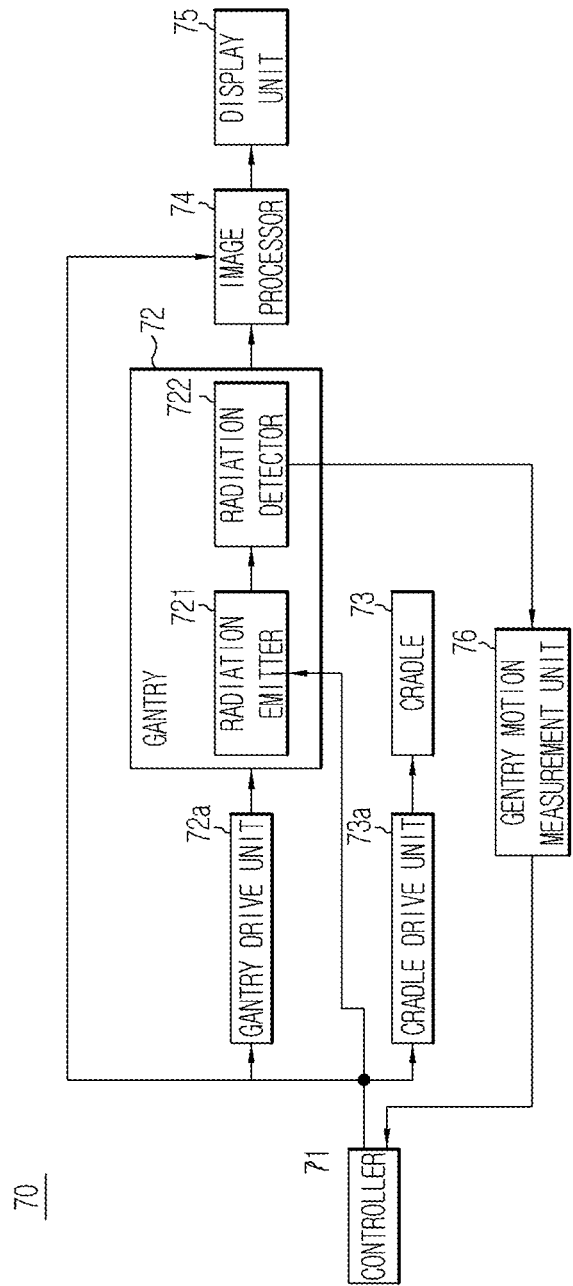
FIG. 13 is a view illustrating a configuration of a computed tomography apparatus.

According to an exemplary embodiment, the radiation imaging apparatus, as exemplarily illustrated in FIG. 13, may be a computed tomography apparatus 70.

FIG. 13 is a view illustrating a configuration of a computed tomography apparatus.

As illustrated in FIG. 13, according to an exemplary embodiment, the computed tomography apparatus 70 includes a controller 71 to control general operations of the computed tomography apparatus 70, a gantry drive unit 72a to drive a gantry 72 upon receiving a control instruction output from the controller 71, a drive unit 73a to drive a cradle 73 upon receiving a control instruction output from the controller 71, a radiation emitter 721 and a radiation detector 722 installed to the gantry 72 to emit radiation to the object ob, a gantry motion measurement unit 76 to measure motion of the gantry 72, for example, a movement angle of the gantry 72 to thereby transmit measured information to the controller 71, and an image processor 74 to generate a radiological image of the object ob. The radiological image generated by the image processor 74 is displayed to the user, for example, a doctor or radiologist via a display unit 75.

Figure 14:
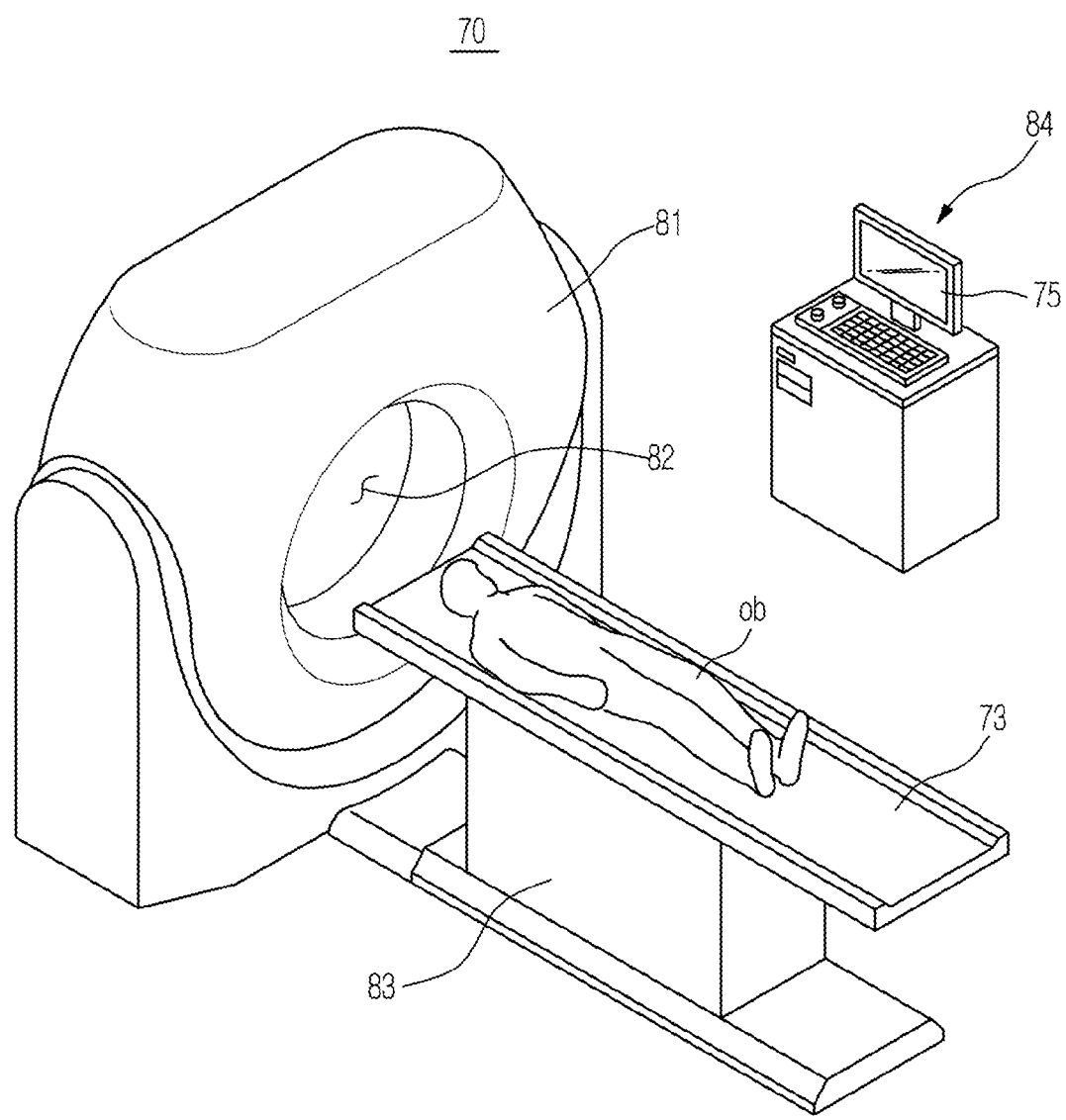
FIGS. 14, 15, and 16 are views illustrating a configuration of a computed tomography apparatus.
Figure 15:
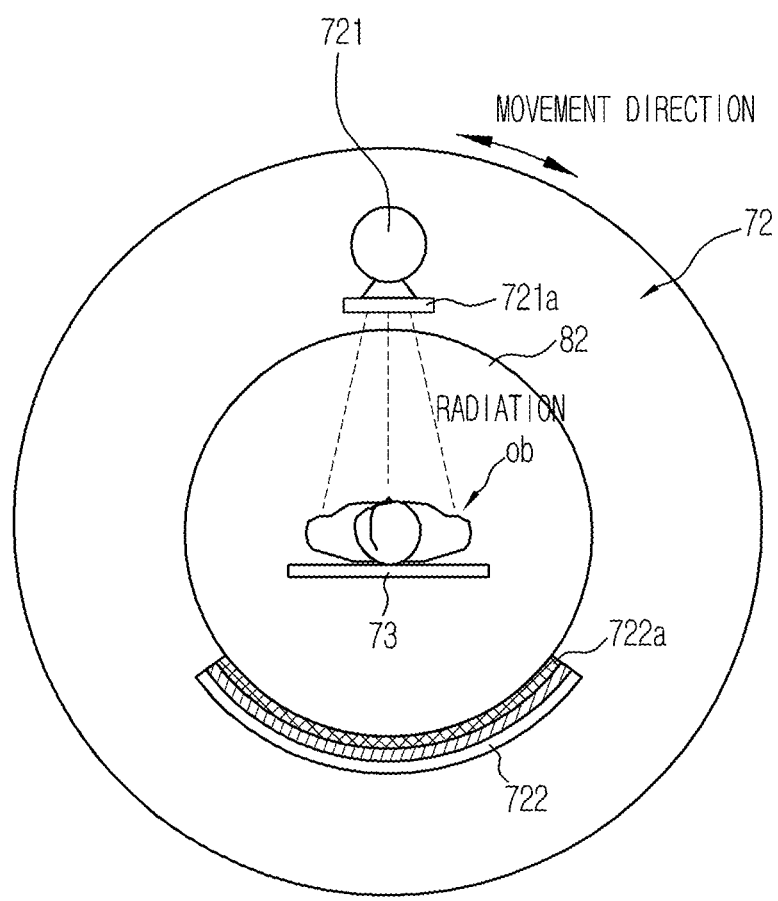
Figure 16:
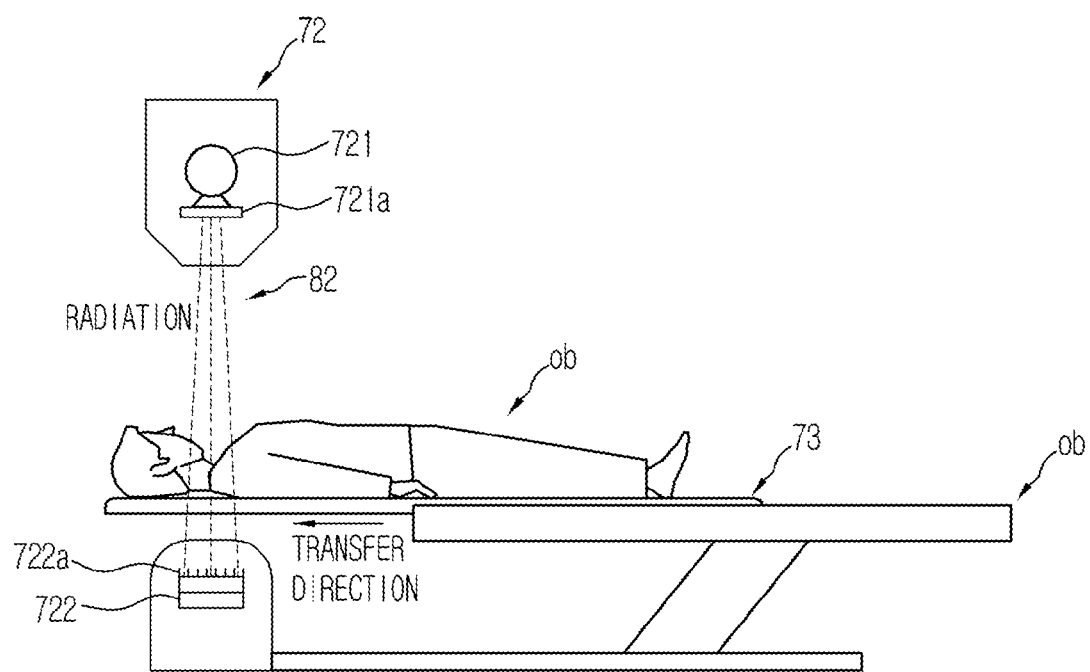
Figure 17:
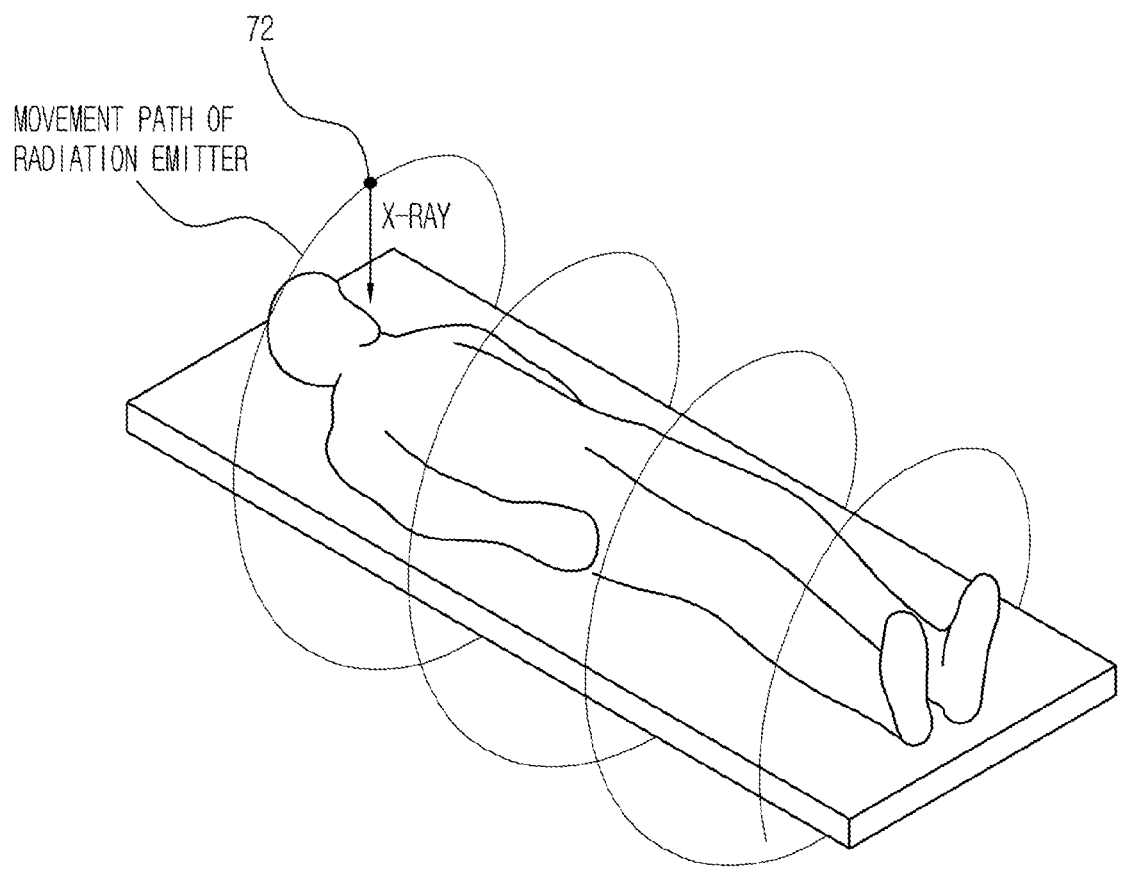
FIGS. 17 and 18 are views explaining radiography by the computed tomography apparatus.
Figure 18:
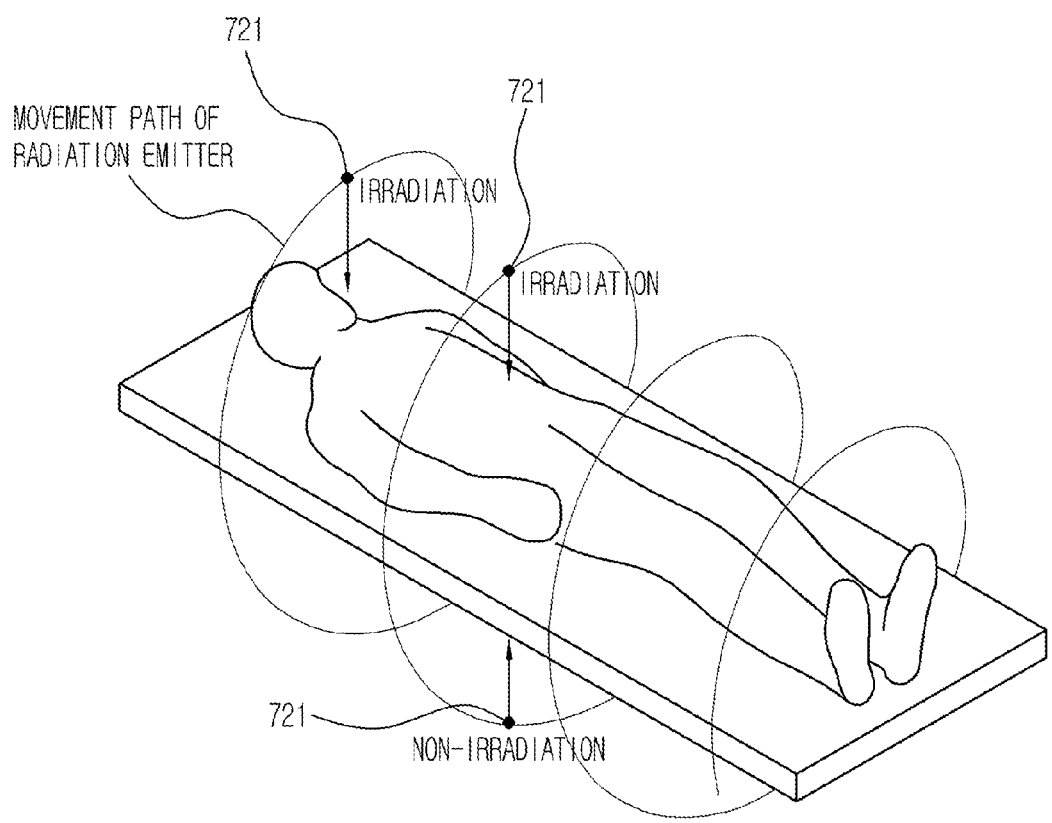

FIGS. 14 to 16 are views illustrating an exemplary embodiment of the computed tomography apparatus, and FIGS. 17 and 18 are views explaining radiography by the computed tomography apparatus.

Referring to FIG. 14, the computed tomography apparatus 70 may include a housing 81 having a central bore 82, a cradle 73 to transfer the object ob placed thereon, and a support structure 83 to support the cradle 73. The cradle 73 that supports the object ob on an upper end thereof is transferred at a predetermined speed into the gantry 72 through the bore 82 of the housing 81 under control of the cradle drive unit 73a. In this case, the object ob placed on the upper end of the cradle 73 is transferred thereby.

According to an exemplary embodiment, the computed tomography apparatus 70 includes an information processing device 84 that displays an image of the object ob and receives various control instructions for the computed tomography apparatus 70 input by the user. The information processing device 84 may include the display unit 75 to display a radiological image to the user, and the above-described controller 71.

Referring to FIGS. 13 to 16, the gantry 72 is installed within the housing 81, and the radiation emitter 721 and the radiation detector 722 are mounted to the gantry 72.

The gantry 72 is rotated by the gantry drive unit 72a that is driven in response to a control instruction of the controller 71. The radiation emitter 721 and the radiation detector 722, mounted to the gantry 72, are fixed at positions facing each other, such that radiation emitted from the radiation emitter 721 may be detected by the radiation detector 722. That is, the radiation detector 722 is installed to the gantry 72 at a position opposite to the radiation emitter 721. A first collimator 721a is installed in a path along which the radiation emitter 721 emits radiation, and serves to filter a radiation emission direction and radiation emission range that the user desires. A second collimator 722a may be installed in a path along which the radiation detector 722 receives radiation and serves to block radiation scattered within the object ob so as to improve accuracy of a radiological image.

If computed tomography is initiated, the gantry 72 initiates rotation according to revolutions per minute preset or input by the user via the external information processing device 84. The radiation emitter 721 emits radiation to the object ob while rotating along with the gantry 72. The radiation detector 721 detects radiation having passed through the object ob or directly reached thereto without passing through the object ob while rotating along with the radiation emitter 721. Then, the radiation detector 721 changes the detected radiation into an electric signal to store the electric signal in the storage element.

Meanwhile, if computed tomography is initiated, as exemplarily illustrated in FIG. 16, the cradle 73 is transferred into the gantry through the bore 82. As such, the radiation emitter 721 emits radiation while being rotated by the gantry 72 relative to the moving object ob.

Accordingly, when viewed on the basis of the object ob, the radiation emitter 721 emits radiation to the object ob while moving along a spiral or a helical path as exemplarily illustrated in FIG. 17. Similarly, when viewed on the basis of the object ob, the radiation detector 722 moves along a spiral or a helical path according to movement of the radiation emitter 721.

The radiation emitter 721, as exemplarily illustrated in FIG. 18, may be controlled to emit radiation to the object only in a direction, and so as not to emit radiation in a direction corresponding to the radiation emission direction, for example, in an opposite direction. For example, under control, the radiation emitter 721 may emit radiation to the object in the particular position l1 as illustrated in FIG. 3A or in the particular irradiation zone a1 as exemplarily illustrated in FIG. 3B, and may not emit radiation to the object ob in the position l4 opposite to the particular position l1 or in the zone opposite to the irradiation zone a1, i.e. in the non-irradiation zone a4.

The radiation emitter 721 may be controlled by the above-described controller 71.

As described above with reference to FIGS. 3C and 3D, the controller 71 may control radiation emission by the radiation emitter 721 by applying or not applying power to the radiation tube of the radiation emitter 721. In other words, the controller 71 may control Power-On/Off of the radiation emitter 721.

To allow the radiation emitter 721 to emit radiation at a position or zone, according to an exemplary embodiment, the gantry motion measurement unit 76 may measure motions of the gantry 72. Specifically, the gantry motion measurement unit 76 may acquire information on a position of the radiation emitter 721 by measuring a rotation angle of the gantry 72 from an initial position thereof. The gantry motion measurement unit 76 transmits information on the acquired position to the controller 71, and the controller 71 generates a control instruction for the radiation emitter 721 based on information on the acquired position to transmit the control instruction to the radiation emitter 721, thereby allowing the radiation emitter 721 to emit radiation to the object ob only at a position or zone.

As described above, radiation emitted by the radiation emitter 721 is detected by the radiation detector 222 to thereby be changed into an electric signal, and the image processor 74 reads out a radiological image from the electric signal. As a result, a radiological image may be acquired by radiation emitted in a position or zone. Meanwhile, as described above with reference to FIGS. 12A to 12F, even when a radiological image is acquired by emitting radiation only in a position or zone, that is, even if the radiation emitter 721 does not emit radiation in a position or zone corresponding to the radiation emission position or zone, radiological images of the object ob in all directions may be acquired.

Figure 19:
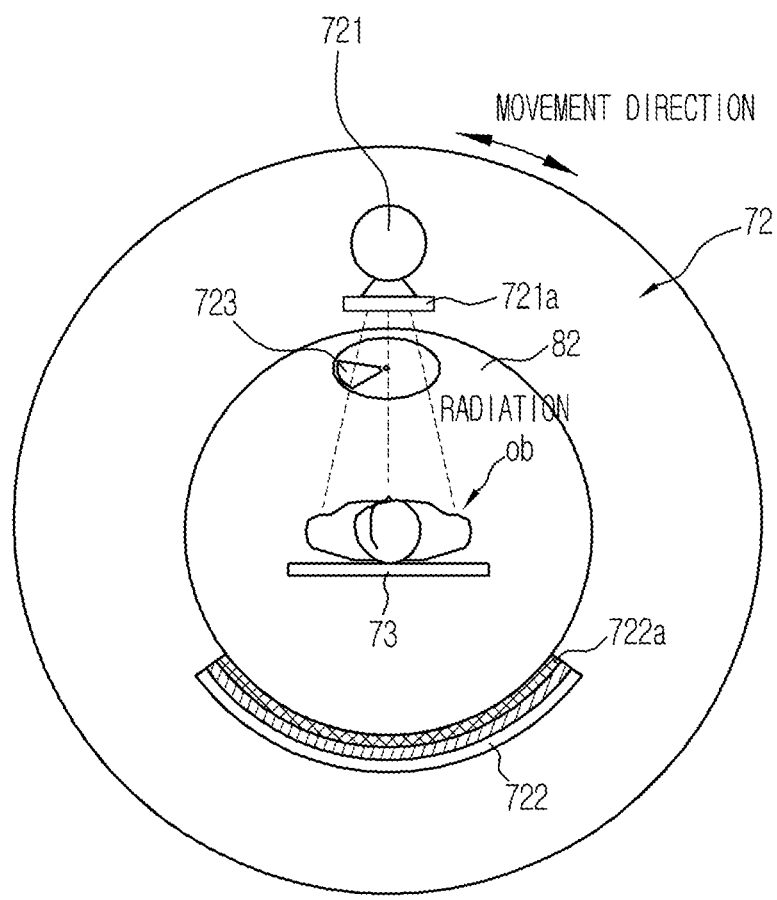
FIGS. 19, 20, and 21 are views illustrating another exemplary embodiment of the computed tomography apparatus.
Figure 20:
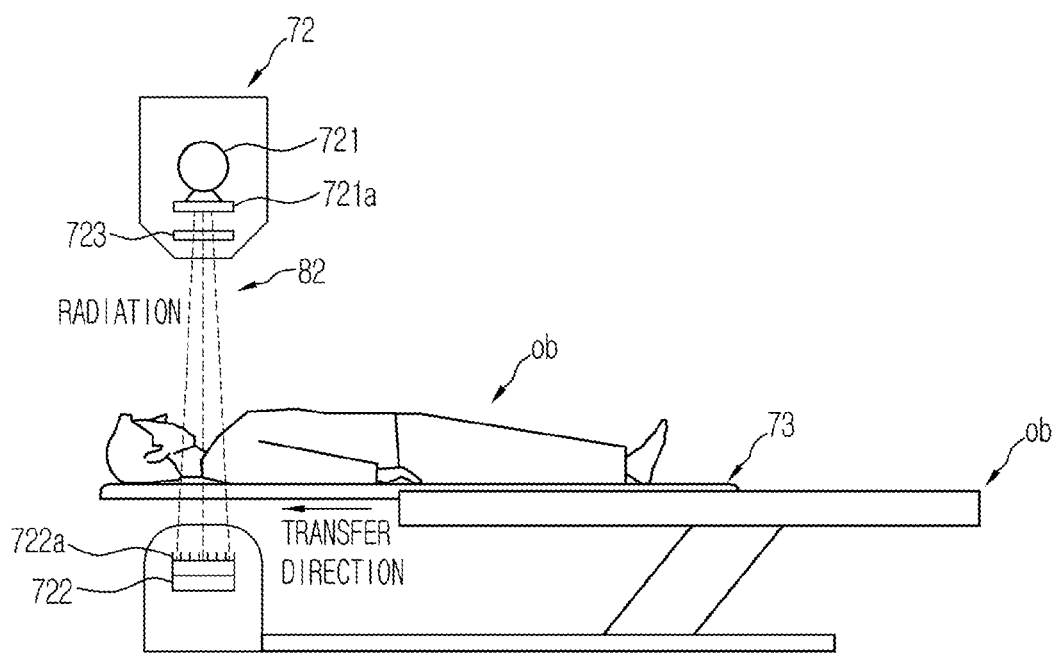
Figure 21:
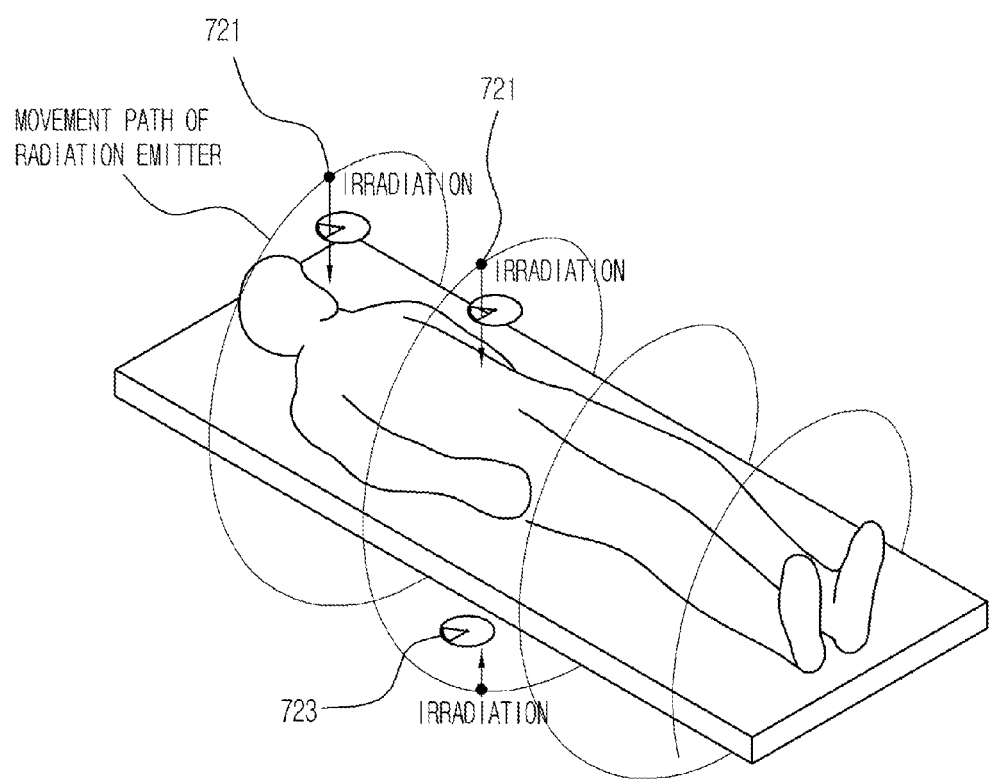

FIGS. 19 to 21 are views illustrating another exemplary embodiment of the computed tomography apparatus.

According to another exemplary embodiment of the computed tomography apparatus 70, as illustrated in FIGS. 19 to 21, a filter 723 may be installed in a radiation emission direction of the radiation emitter 721, i.e. in a path along which the radiation emitter 721 emits radiation. The filter 723 controls emission of radiation to the object ob by passing or blocking the radiation from the radiation emitter 721. In particular, the filter 723 may pass or block radiation when the radiation emitter 721 is located at a position or zone.

The filter 723 may have various shapes as illustrated in FIGS. 5A to 5D and FIGS. 6A and 6B. In particular, according to an exemplary embodiment, the filter 723 may include at least one opening 141 to pass radiation, and may rotate about the rotating shaft 143 located inside or outside of the filter 723. A rotational angular speed of the filter 723 is set to correspond to an angular speed of the radiation emitter 721 that moves along a circular or spiral movement path. In addition, the rotational angular speed of the filter 723 may be set, as described above, based on the number of openings 141 for passage of radiation, the number of times radiation is emitted while the radiation emitter 721 moves along a circular movement path once, and the sizes of irradiation zones and non-irradiation zones.

Accordingly, as exemplarily illustrated in FIG. 21, despite that the radiation emitter 721 continuously emits radiation, the filter 723 may cause radiation to be emitted to the object ob only in some directions by blocking radiation in a particular position or zone, in particular, in a position or zone opposite to the emission position or zone.

In the case of some conventional radiation tomography apparatuses, the gantry 72, i.e. the radiation emitter 721 acquires a radiological image of 800 to 1400 frames while rotating for about 250 ms, and therefore there is difficulty in controlling the radiation emitter 721 to periodically emit radiation. This is because control of periodic generation of radiation may require application of a high voltage to the radiation emitter 721, more particularly to the radiation tube for 0.2 μs.

However, when using the filter 723, emission of radiation to the object ob may be controlled even by continuously applying a voltage to the radiation emitter 721, rather than periodically applying a voltage to the radiation emitter 721. In other words, emission of radiation to the object ob may be controlled even in the case in which the radiation emitter 721 continuously generates radiation, rather than periodically generating radiation.

In other words, as exemplarily illustrated in FIG. 3C, it may be possible to control emission of radiation to the object ob in a pulse form.

Accordingly, a radiation tomography apparatus that may not control periodic generation of radiation may realize periodic emission of radiation to the object ob.

Radiation, which has emitted by the radiation emitter 721 and passed through the filter 723, may be detected by the radiation detector 722 and changed into an electric signal. The changed electric signal is read out by the image processor 74, and the image processor 74 generates a radiological image using the electric signal. Consequently, a radiological image may be acquired by radiation emitted in a position or zone. In this case, as described above with reference to FIGS. 12A to 12F, although the radiation emitter 721 emits radiation only in a position or zone, and does not emit radiation in a position or zone corresponding to the position or zone, radiological images of the object ob in all directions may be acquired.

Figure 22A:
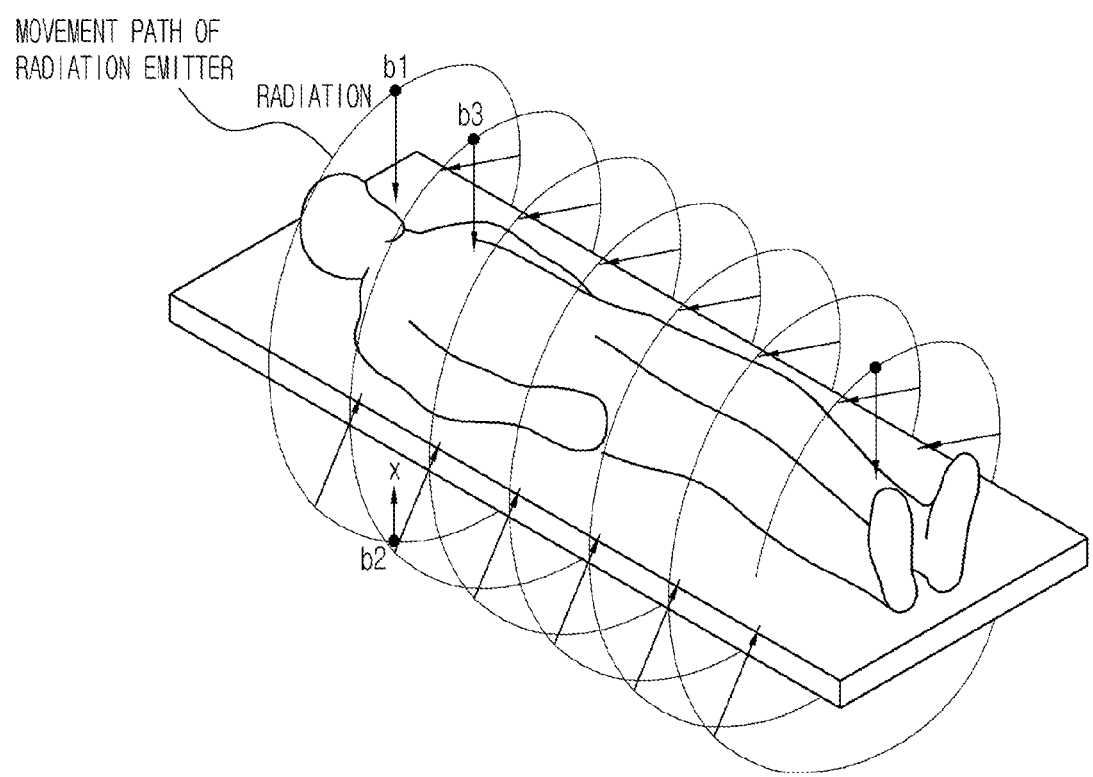
FIGS. 22A, 22B, and 22C are views explaining generation of radiological images according to an exemplary embodiment.
Figure 22B:
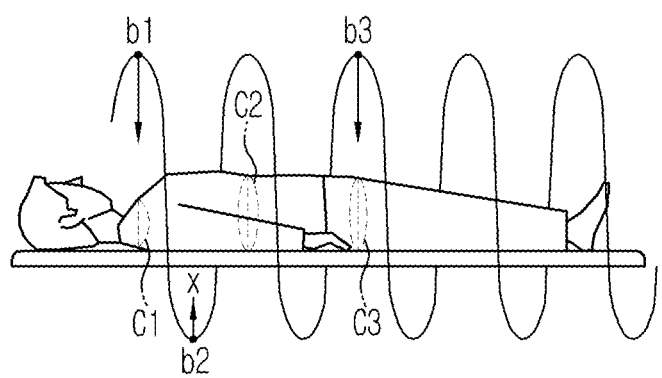
Figure 22C:
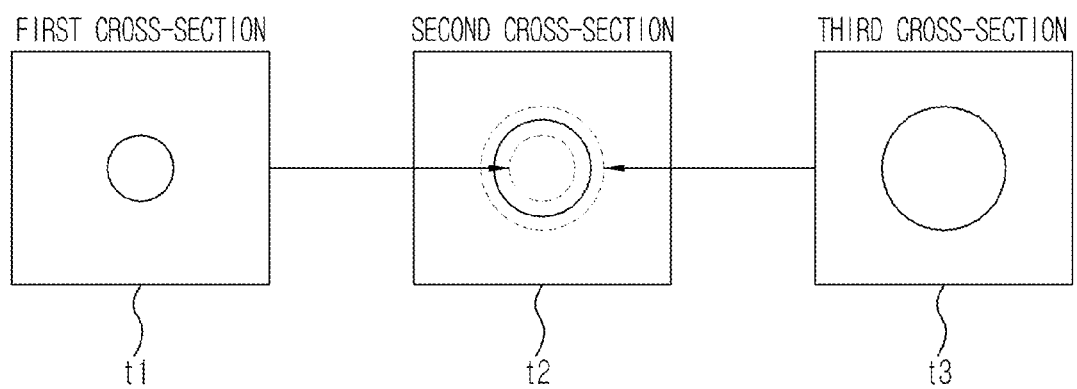

FIGS. 22A to 22C are views explaining generation of radiological images according to an exemplary embodiment.

As described above, radiation emitted from the radiation emitter 721 is detected and changed into an electric signal by the radiation detector 722, and the image processor 74 reads out a radiological image from the electric signal. In this case, the image processor 74, as described above, may acquire radiological image data in a radiation emission direction as well as radiological image data in a direction corresponding to the radiation emission direction. However, in a spiral or a helical scan method, since the object ob is moved in a direction, for example, in a transfer direction, radiological image data acquired in a radiation emission direction may differ from radiological image data acquired in a direction corresponding to the radiation emission direction.

For example, as illustrated in FIGS. 22A and 22B, since the radiation emitter 721 emits radiation only in a position, for example, in a position b1 or b3 or in a zone while spirally rotating about the object ob, image data for a first cross-section c1 in the position b1 or a third cross-section c3 in the position b3 may be acquired, but a radiological image in a non-irradiation position, for example, in a position b2 or other positions, for example, accurate image data for a second cross-section c2 may not be acquired.

According to an exemplary embodiment, as exemplarily illustrated in FIG. 22C, an image t2 of the second cross-section c2 may be acquired using an image t1 of the first cross-section c1 and an image t3 of the third cross-section c3. In addition, radiological image data that will be acquired when radiation is emitted in the position b2 may be acquired using the image t2 of the second cross-section c2.

Image data on the second cross-section c2 may be acquired using an intermediate value between image data on the first cross-section c1 and image data on the third cross-section c3, or by applying weighting to each image data and combining the image data. In this case, an image of the second cross-section c2 may be acquired by comparing the image t1 of the first cross-section c1 and the image t3 of the third cross-section c3 with each other and using a motion prediction method.

A plurality of radiological images acquired as described above, for example, a plurality of image data including image data on the first cross-section c1, image data on the second cross-section c2 and image data on the third cross-section c3 are combined by the image processor 74, whereby a cross-sectional image of the object ob is acquired and is displayed to the user via the display unit 75. Accordingly, a radiological tomographic image without data loss may be acquired even via radiation emission within a partial zone, i.e. an irradiation zone.

Figure 23:
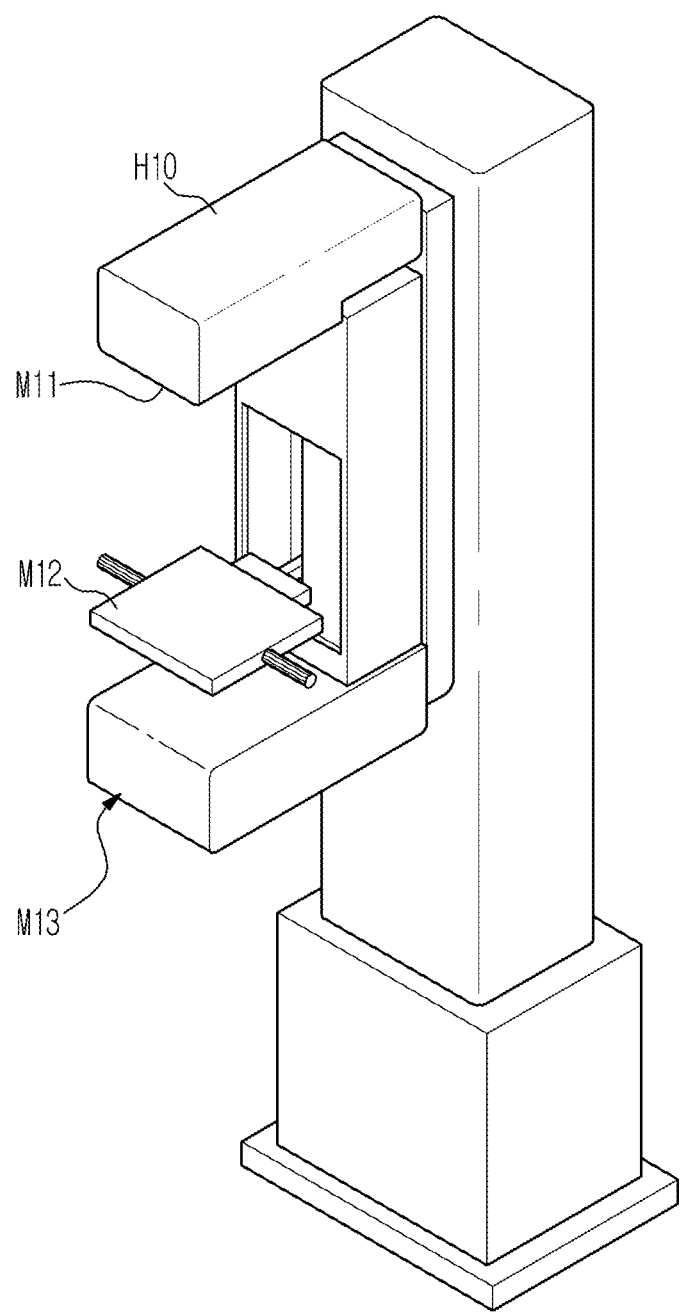
FIGS. 23, 24, and 25 are views explaining an exemplary embodiment of a Full Field Digital Mammography (FFDM) apparatus.

In another exemplary embodiment, the radiation imaging apparatus may be a Full Field Digital Mammography (FFDM) apparatus as exemplarily illustrated in FIG. 23.

Figure 24:
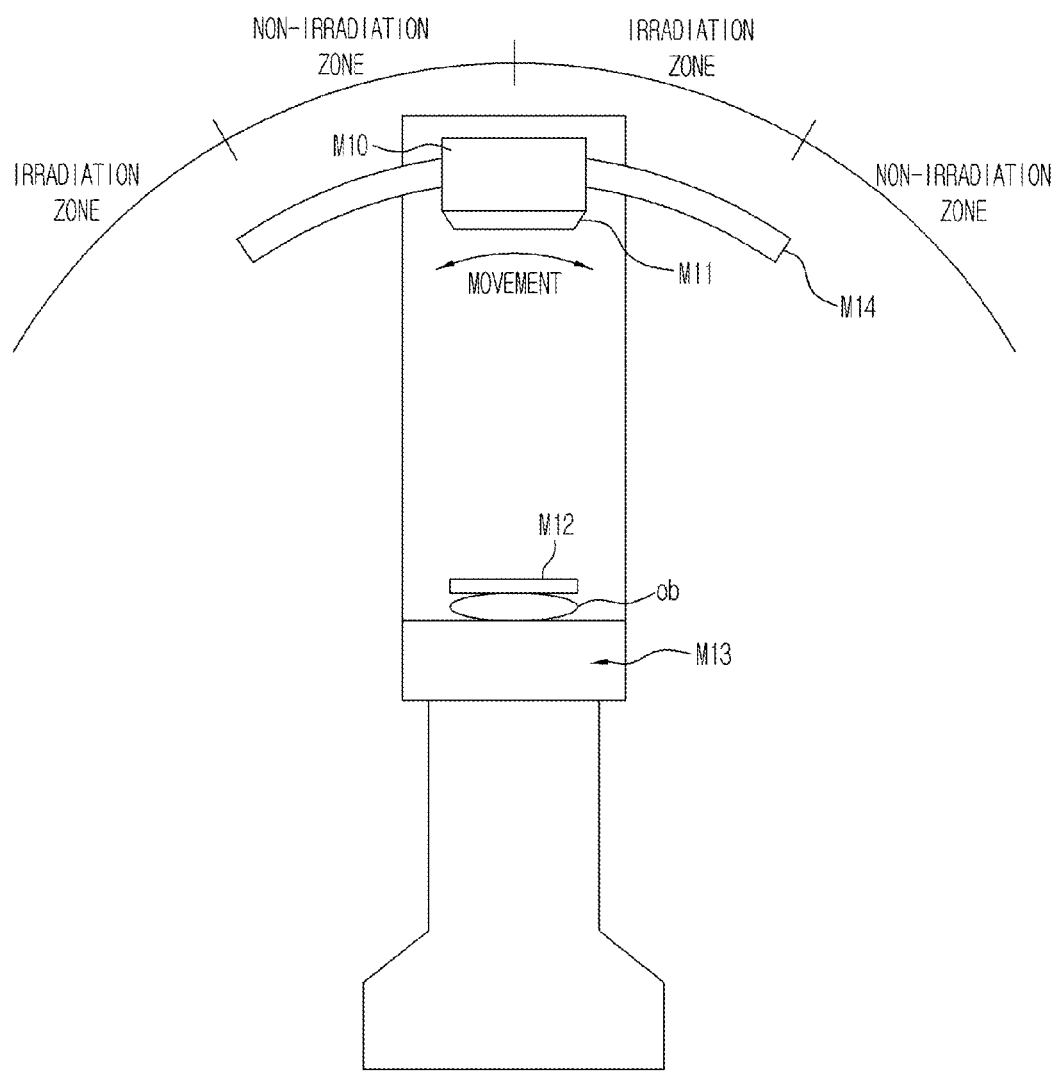
Figure 25:
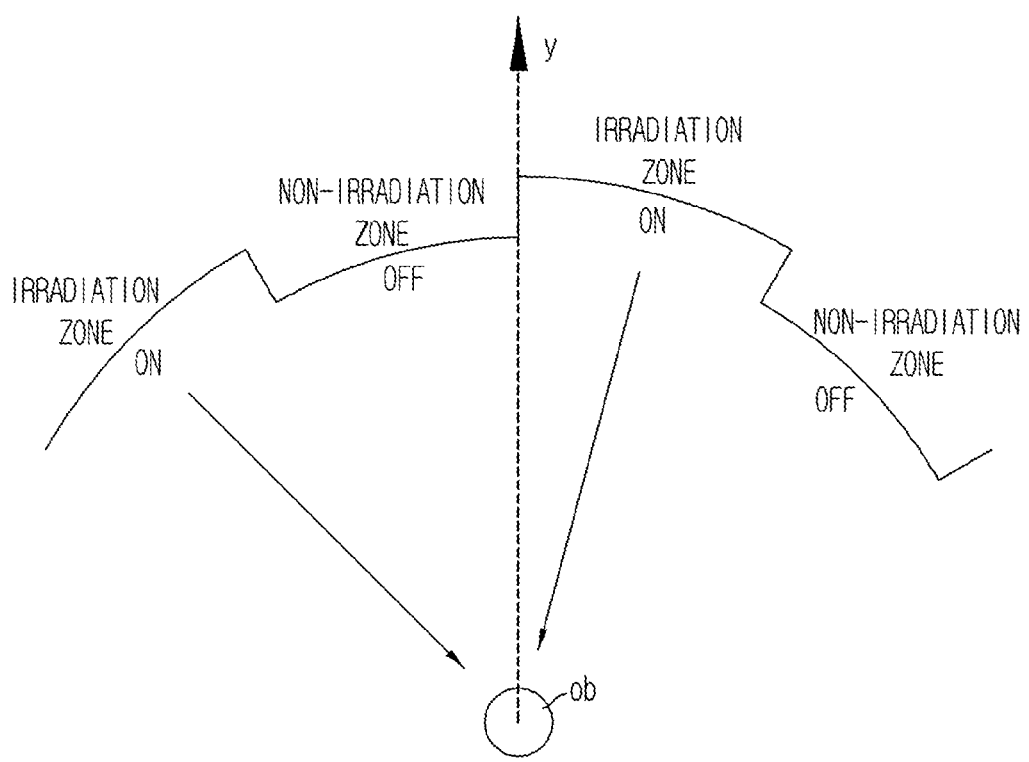

FIGS. 23 to 25 are views explaining an exemplary embodiment of the FFDM apparatus.

As exemplarily illustrated in FIGS. 23 and 24, the FFDM apparatus may include a head m10 to which a radiation emitter m11 is installed, a cradle m13 on which the object ob, for example, the breast is placed, and a compressor m12 to compress the object ob, for example, the breast.

The radiation emitter m11, installed to the head m10, may emit radiation toward the cradle m13. In one exemplary embodiment, the head m10, as exemplarily illustrated in FIG. 24, may be moved in at least one direction along a movement path that is formed on a transfer device, such as a rail m14. In this case, the radiation emitter m11 installed to the head m10 may be moved simultaneously with movement of the head m10.

The movement path of the head m10 may be divided into a plurality of zones. The plurality of zones may be any one of an irradiation zone and a non-irradiation zone. The radiation emitter m11 emits radiation to the object ob in the irradiation zone, and does not emit radiation to the object ob in the non-irradiation zone by stopping emission of radiation by the radiation emitter m11.

In one exemplary embodiment, the plurality of zones may be arranged such that one irradiation zone corresponds to one non-irradiation zone. In addition, a zone corresponding to a non-irradiation zone among the plurality of zones may be an irradiation zone. For example, as exemplarily illustrated in FIG. 25, an irradiation zone and a non-irradiation zone may be symmetrical to each other about an axis, for example, the Y-axis.

The compressor m12 may compress the object ob, for example, the breast, to ensure radiation of emission to a greater area of the object ob.

The object ob, for example, the breast is placed on the cradle m13. The cradle m13 may further include a radiation detector to detect radiation emitted from the radiation emitter m11. The radiation detector may include a radiation detection panel. The radiation detector may be installed inside or outside of the cradle m13, and may be installed, for example, to an outer surface of the cradle m13 on which the breast is placed.

Referring to FIGS. 24 and 25, the radiation emitter m11 of the FFDM apparatus may emit radiation to the object ob only in a zone, for example, in an irradiation zone, and may not emit radiation to the object ob in another zone, for example, in a non-irradiation zone. In this case, if the radiation emitter m11 is located in the irradiation zone, as described above, a voltage is applied to the radiation tube of the radiation emitter m11 (power-on state), whereby the radiation emitter m11 emits radiation to the object ob. In addition, if the radiation emitter m11 is moved to enter the non-irradiation zone, a voltage is no longer applied to the radiation tube of the radiation emitter m11 (power-off state), whereby the radiation emitter m11 stops emission of radiation. If the radiation emitter m11 again enters the irradiation zone, a voltage is again applied to the radiation tube of the radiation emitter m11 (power-on state), whereby the radiation emitter m11 restarts emission of radiation.

In one exemplary embodiment, if radiation is emitted only in an irradiation zone, radiological image data only in the irradiation zone may be acquired, but acquisition of radiological image data in the non-irradiation zone may be impossible.

In this case, in one exemplary embodiment, radiological image data in the non-irradiation zone may be calculated based on radiological image data in the irradiation zone by the above-described reverse image generator 32. In addition, it may be possible to acquire radiological image data in all zones by combining radiological image data in the irradiation zone with the calculated radiological image data in the non-irradiation zone. In this way, it may be possible to generate an image of the object ob using the acquired radiological image data.

Figure 26:
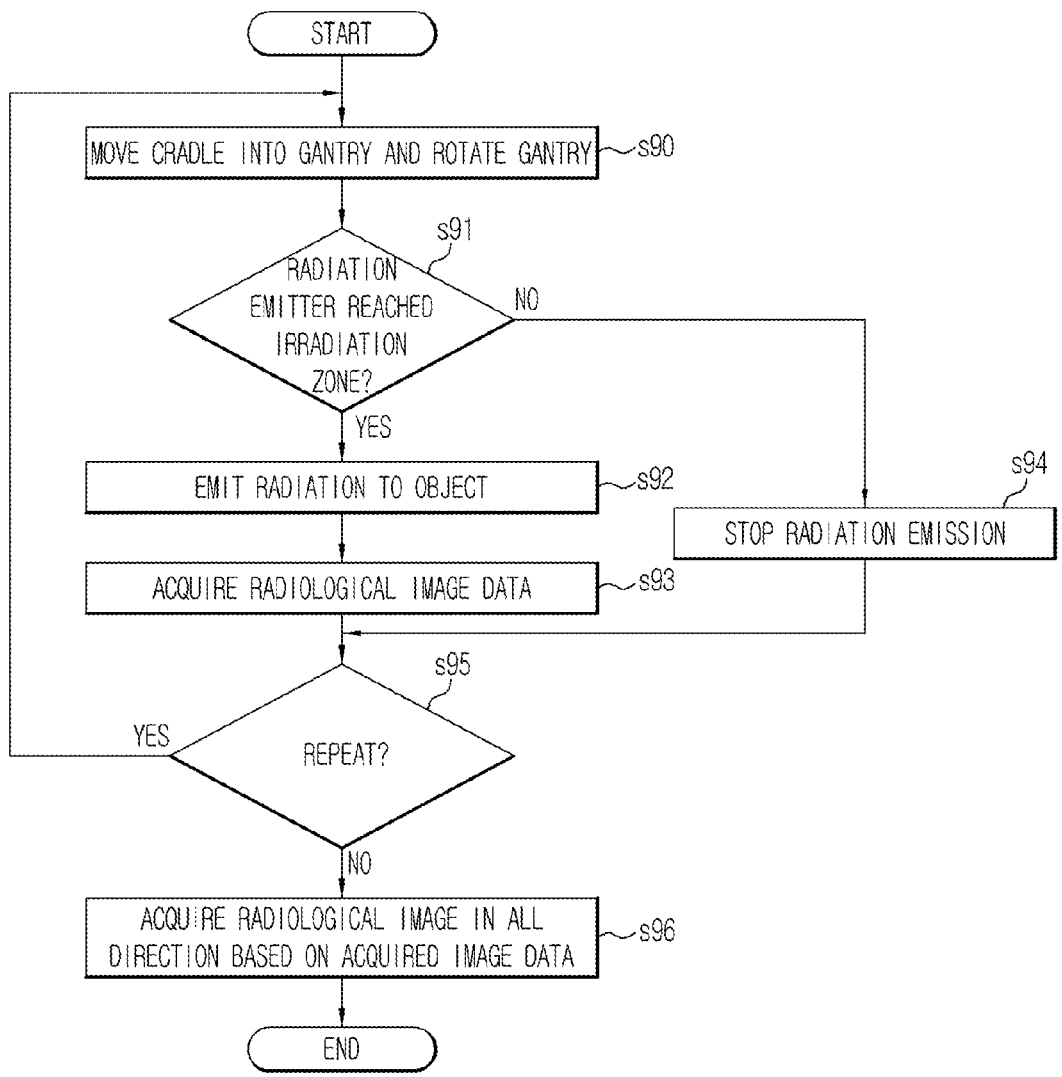
FIGS. 26 and 27 are flowcharts illustrating various exemplary embodiments of a radiological image generation method.
Figure 27:
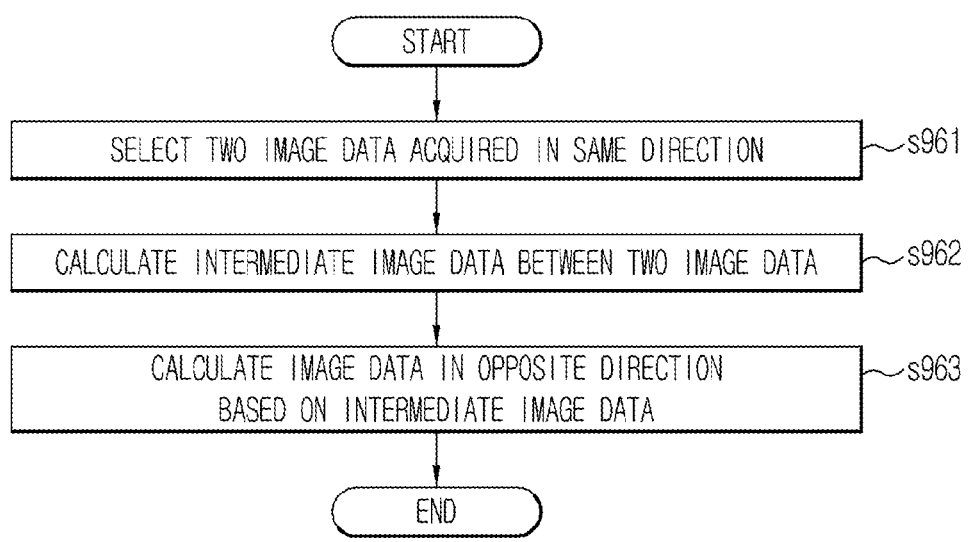

FIGS. 26 and 27 are flowcharts illustrating various exemplary embodiments of a radiological image generation method.

As exemplarily illustrated in FIG. 26, according to an exemplary embodiment of a radiological image generation method using a radiation imaging apparatus, for example, a computed tomography apparatus, if radiation imaging is initiated, an object ob is placed on a cradle and is moved through a bore of the computed tomography apparatus. In addition, rotation of a gantry is initiated. A radiation emitter is moved via rotation of the gantry (s90).

If the radiation emitter reaches an irradiation zone via movement thereof (s91), the radiation emitter begins to emit radiation to the object (s92). In this case, a non-irradiation zone is located opposite to the irradiation zone.

If the emitted radiation reaches a radiation detector after passing through the object, the radiation detector detects the radiation and changes the radiation into an electric signal. The electric signal or the image represented by the electrical signal is stored as image data on the irradiation zone (s93). In this case, as described above with reference to FIGS. 12A to 12F, a radiological image in the irradiation zone as well as a radiological image in a corresponding non-irradiation zone may be acquired.

The radiation emitter continuously emits radiation while being moved to acquire data on a plurality of images. Then, if the radiation emitter reaches the non-irradiation zone, the radiation emitter stops emission of radiation (s94). The non-irradiation zone is a zone corresponding to the irradiation zone. For example, the non-irradiation zone may be located symmetrical to the irradiation zone about a point or axis.

Through rotation of the gantry, Operations s90 to s94 are repeated to acquire image data in all zones (s95).

Radiological images in all directions are acquired using image data acquired based on radiation emitted in all zones (s96). According to exemplary embodiments, based on image data acquired by emitting radiation in a particular direction, a reverse image may be acquired using data on an image captured in a direction opposite to the particular direction (s96). That is, based on image data acquired in the irradiation zone, an image of the non-irradiation zone corresponding to the irradiation zone may be acquired.

Meanwhile, in the case of using a spiral or a helical scan method, a radiological image in a non-irradiation zone corresponding to an irradiation zone may differ from a radiological image acquired by radiation emitted in the non-irradiation zone. In this case, as exemplarily illustrated in FIG. 27, a radiological image in the non-irradiation zone may be calculated using a radiological image acquired by emitting radiation in the irradiation zone.

According to an exemplary embodiment, first, at least two images acquired via radiation emission in the same direction are selected from among image data in the plurality of irradiation zones (s961). In this case, although the two image data may be images acquired by emitting radiation in the same radiation emission position or zone, it may be unnecessary to emit radiation in the same direction.

Then, intermediate image data is acquired by taking an intermediate value of the two image data or by applying weighting to the two image data and combining the two image data (s962). The intermediate image data, for example, may be data on the image t2 of the second cross-section c2 as exemplarily illustrated in FIG. 22C.

At least one image data in a direction opposite to the radiation emission direction is calculated based on the acquired intermediate image data (s963). As described above, since there is non-emission opposite to the irradiation zone, a reverse image may not be acquired via radiation emission. In addition, in the case of a computed tomography apparatus, this is similar to the case in which the radiation emitter emits radiation to the object while spirally moving around the object, and therefore a more accurate reverse image may be acquired when calculation of intermediate image data proceeds.

As is apparent from the above description, through a radiation imaging apparatus, a computed tomography apparatus, and a radiation imaging method, it may be possible to acquire radiological images in all directions of an object even when emitting radiation in some directions or zones.

Even when a radiation emitter emits radiation in a pulse form, or even when the object is irradiated in a pulse form, not only data on an image of a partial angular range in which radiation emission is performed, but also data on radiological images in all directions in which radiation emission is not performed, may be acquired, which provides sufficient radiological image data.

Accordingly, it may be unnecessary to directly emit radiation to the object in all directions, which may allow the object, in particular, a human body to be exposed to less radiation. In particular, it may be possible to reduce radiation exposure of the object by half in a direction opposite to a radiation emission direction as radiation is not emitted to the object in the direction opposite to the radiation emission direction.

In a computed tomography apparatus, it may be possible to generate a successive cross-sectional image of the object even if radiation is emitted in positions or zones.

Although the exemplary embodiments have been shown and described, it would be appreciated by those skilled in the art that changes may be made in these exemplary embodiments without departing from the principles and spirit of the invention, the scope of which is defined in the claims and their equivalents.

What is claimed is:

1. A radiation imaging apparatus comprising:
    an emitter configured to move along a path around an object and to emit radiation toward the object when the emitter is located in a plurality of first portions of the path; and
    a controller configured to control the emitter to stop a radiation emission, when the emitter is located in a plurality of radiation reception zones which are zones in which a detector is located when the emitter emits the radiation toward the object in the plurality of first portions of the path,
    wherein the radiation emitted by the emitter comprises X-ray radiation, and
    at least one of the plurality of radiation reception zones comprises a sub-zone in which the emitter emits the radiation decreasingly or increasingly, when the emitter is located in the at least one of the plurality of radiation reception zones.

2. The apparatus according to claim 1, wherein the controller is configured to control the emitter to emit the radiation decreasingly in the sub-zone before the emitter stops the radiation emission in at least one of the plurality of radiation reception zones.

3. The apparatus according to claim 1, wherein the controller is configured to control the emitter to emit the radiation increasingly in the sub-zone before the emitter re-emits the radiation in an outside of at least one of the plurality of radiation reception zones.

4. The apparatus according to claim 1, wherein the sub-zone is located in at least one of both boundaries of at least one of the plurality of radiation reception zones.

5. The apparatus according to claim 1, wherein the detector is configured to detect the radiation emitted from the emitter and generate signals based on the detected radiation, and
    the apparatus further comprises an image processor configured to read out a radiological image from the signals.

6. The apparatus according to claim 1, wherein the emitter moves about the object at an angular speed, and
    the controller determines whether the emitter emits the radiation based on the angular speed of the emitter.

7. The apparatus according to claim 1, further comprising a filter disposed in a radiation emission path along which the radiation is emitted by the emitter, to pass or to block all of the radiation or a portion of the radiation emitted by the emitter.

8. The apparatus according to claim 1, wherein the plurality of first portions correspond to a plurality of radiation emission zones, and
    the plurality of radiation emission zones and the plurality of radiation reception zones are disposed repeatedly and alternatively on the path of the emitter corresponding to a gantry rotation angle of 360°.

9. The apparatus according to claim 8, wherein the plurality of radiation emission zones and the plurality of radiation reception zones are disposed symmetrically on the path, with respect to the object.

10. The apparatus according to claim 8, wherein the plurality of radiation emission zones are disposed opposite to the plurality of radiation reception zones and made complimentary to the plurality of radiation reception zones.

11. A radiation imaging apparatus comprising:
an emitter configured to move along a path about an object and emit radiation,
wherein the radiation emitted by the emitter comprises X-ray radiation,
the path about the object comprises a plurality of irradiation zones in which the emitter emits the radiation and a plurality of non-irradiation zones in which the emitter stops a radiation emission, and
the plurality of non-irradiation-zones are opposite to the plurality of irradiation zones respectively, wherein at least one of the plurality of non-irradiation zones comprises at least one sub-zone in which the emitter emits the radiation decreasingly or increasingly.

12. The apparatus according to claim 11, wherein the emitter is moved along the path defined about the object at an angular speed.

13. The apparatus according to claim 12, further comprising a controller to control an operation of the emitter based on the angular speed of the emitter, a duration of the plurality of irradiation zones, or a duration of the plurality of non-irradiation zones.

14. A radiation imaging apparatus comprising:
a radiation emitter configured to move along a first path about an object and to emit radiation, the first path having a plurality of first portions in which the radiation is emitted toward the object; and
a filter disposed in a second path along which the radiation is emitted by the radiation emitter, to pass or to block all of the radiation or a portion of the radiation emitted from the radiation emitter, wherein the filter blocks all of the radiation or the portion of the radiation emitted from the radiation emitter when the radiation emitter is located in a plurality of radiation reception zones which are zones in which a detector is located when the radiation emitter emits the radiation toward the object in the plurality of first portions of the first path,
the radiation emitted by the radiation emitter comprises X-ray radiation, and
at least one of the plurality of radiation reception zones comprises a sub-zone in which the radiation emitter emits the radiation decreasingly or increasingly, when the radiation emitter is located in at least one of the plurality of radiation reception zones.

15. The apparatus according to claim 14, wherein the filter comprises at least one opening to pass the radiation.

16. The apparatus according to claim 14, wherein an angular speed of the filter is determined based on a number of openings formed in the filter to pass the radiation, an angular speed of the radiation emitter, a number of times the radiation is emitted during one rotation of the radiation emitter, sizes of the plurality of first portions, respectively, or sizes of the plurality of radiation reception zones, respectively.

17. A radiological image acquisition method using a computed tomography apparatus, the method comprising:
performing a radiation imaging operation by controlling an emitter to move along a path around an object; and
acquiring a radiological image based on the radiation imaging operation,
wherein the performing the radiation imaging operation comprises emitting radiation when the emitter is located at a plurality of first portions of the path, and stopping a radiation emission when the emitter is located in a plurality of radiation reception zones which are zones in which a detector is located when the emitter emits the radiation toward the object in the plurality of first portions of the path,
the emitting the radiation comprises emitting the radiation decreasingly or increasingly in a sub-zone which is a portion of at least one of the plurality of radiation reception zones, and
the radiation emitted by the emitter comprises X-ray radiation.

18. The method according to claim 17, wherein the performing the radiation imaging operation further comprises:
emitting the radiation toward the object and acquiring image data until the emitter reaches at least one of the plurality of radiation reception zones;
decreasing a dose of the radiation when the emitter is located in a first sub-zone of at least one of the plurality of radiation reception zones;
stopping the radiation emission when the emitter is located in a second sub-zone of the plurality of radiation reception zones; and
increasing a dose of the radiation when the emitter is located in a third sub-zone of at least one of the plurality of radiation reception zones,
wherein the first sub-zone, the second sub-zone and the third sub-zone are portions of at least one of the plurality of radiation reception zones.

19. The method according to claim 17, wherein the performing the radiation imaging operation further comprises:
passing the radiation emitted toward the object through a filter until the emitter reaches at least one of the plurality of radiation reception zones; and
blocking all of the radiation or a portion of the radiation emitted toward the object, using the filter when the emitter is located in the at least one of the plurality of radiation reception zones.

20. A radiation imaging apparatus comprising:
an emitter configured to move along a path around an object and to emit radiation toward the object when the emitter is located at a plurality of first portions of the path; and
a controller configured to control the emitter to change a dose of the radiation emitted by the emitter and to stop a radiation emission, when the emitter is located in a plurality of radiation reception zones which are zones in which a detector is located when the emitter emits the radiation toward the object in the plurality of first portions of the path,
wherein the radiation emitted by the emitter comprises X-ray radiation.

* * * * *